(12) United States Patent
Sivathanu et al.

(10) Patent No.: US 9,459,216 B2
(45) Date of Patent: Oct. 4, 2016

(54) METHOD FOR CHARACTERIZING FLAME AND SPRAY STRUCTURES IN WINDOWLESS CHAMBERS

(71) Applicant: En'Urga, Inc., West Lafayette, IN (US)

(72) Inventors: Yudaya Raju Sivathanu, West Lafayette, IN (US); Jongmook Lim, West Lafayette, IN (US); Ye Mi, West Lafayette, IN (US)

(73) Assignee: En'Urga, Inc., West Lafayette, IN (US)

( * ) Notice: Subject to any disclaimer, the term of this patent is extended or adjusted under 35 U.S.C. 154(b) by 537 days.

(21) Appl. No.: 13/798,403

(22) Filed: Mar. 13, 2013

(65) Prior Publication Data

US 2013/0195245 A1 Aug. 1, 2013

Related U.S. Application Data

(63) Continuation-in-part of application No. 12/561,739, filed on Sep. 17, 2009, now abandoned.

(60) Provisional application No. 61/142,505, filed on Jan. 5, 2009.

(51) Int. Cl.
*G01N 23/04* (2006.01)
*G01N 9/24* (2006.01)

(52) U.S. Cl.
CPC ............ *G01N 23/04* (2013.01); *G01N 9/24* (2013.01); *G01N 2223/601* (2013.01); *G01N 2223/633* (2013.01); *G01N 2223/638* (2013.01)

(58) Field of Classification Search
CPC .. G01N 23/04; G01N 9/24; G01N 2223/601; G01N 2223/638; G01N 2223/633
See application file for complete search history.

(56) References Cited

U.S. PATENT DOCUMENTS

| | | | |
|---|---|---|---|
| 4,092,537 A | 5/1978 | Stewart | |
| 4,196,352 A | 4/1980 | Berninger et al. | |
| 4,603,257 A | 7/1986 | Packer et al. | |
| 5,245,648 A | 9/1993 | Kinney et al. | |
| 5,331,155 A * | 7/1994 | Blauch | G01V 5/08 378/4 |

(Continued)

OTHER PUBLICATIONS

Ning, Wei, Development of a Next-generation Spray and Atomization Model Using an Eulerian-Lagrangian Methodology, 2007, pp. 1 and 42-43.*

(Continued)

*Primary Examiner* — Glen Kao
(74) *Attorney, Agent, or Firm* — Brinks Gilson & Lione

(57) ABSTRACT

Method for detecting variations in gas density within a volume surrounded by a closed metal wall opaque to optical light includes a source of x-rays positioned at a selected location outside the closed metal wall. Positioning a detector outside the closed metal wall at a location suitable to detect x-rays from the source passing entirely through a portion of the volume surrounded by the closed metal wall. Providing the detector with a plurality of sensors arranged in at least one row to capture a dimensionally distributed view of detected x-rays. Coupling a processor to an output of the detector to analyze the data which can be displayed in a suitable graphical or pictorial presentation, including processing the data to correct for any beam hardening of the x-rays as they pass through the closed metal wall, to apply the Maximum Likelihood Estimation method to generate on the display a reconstructed image of the gas density, and to use Inverse Radon Transforms for deconvolution. A dopant can be added to enhance the interaction with the x-rays.

20 Claims, 20 Drawing Sheets

(56) References Cited

U.S. PATENT DOCUMENTS

| | | | |
|---|---|---|---|
| 5,689,540 | A | 11/1997 | Stephenson et al. |
| 5,822,390 | A | 10/1998 | Hewitt et al. |
| 5,982,847 | A * | 11/1999 | Nelson ............... G01N 33/2858 378/45 |
| 6,097,786 | A | 8/2000 | Groves et al. |
| 6,111,511 | A | 8/2000 | Sivathanu et al. |
| 6,184,989 | B1 | 2/2001 | Sivathanu et al. |
| 6,292,756 | B1 | 9/2001 | Lievois et al. |
| 6,355,930 | B1 | 3/2002 | Sivathanu et al. |
| 6,370,486 | B1 | 4/2002 | Sivathanu |
| 6,393,375 | B1 | 5/2002 | Sivathanu |
| 6,782,150 | B2 | 8/2004 | Davis et al. |
| 7,075,062 | B2 | 7/2006 | Chen et al. |
| 7,136,451 | B2 | 11/2006 | Naidu et al. |
| 7,266,178 | B2 | 9/2007 | Grodzins |
| 7,298,826 | B2 | 11/2007 | Inazuru |
| 7,316,166 | B2 | 1/2008 | Atkinson |
| 7,352,885 | B2 | 4/2008 | Eberhard et al. |
| 7,402,796 | B2 | 7/2008 | Fitzgerald |
| 7,469,188 | B2 | 12/2008 | Wee |
| 7,474,971 | B2 | 1/2009 | Hu et al. |
| 2003/0147489 | A1 * | 8/2003 | Bijjani ............... G01N 23/046 378/4 |
| 2003/0215052 | A1 | 11/2003 | Grodzins |
| 2005/0152590 | A1 | 7/2005 | Thieret et al. |
| 2005/0226364 | A1 * | 10/2005 | Bernard De Man .. A61B 6/032 378/9 |
| 2007/0291898 | A1 | 12/2007 | Groves et al. |

OTHER PUBLICATIONS

Kastengren et al., X-Ray Radiography Measurements of Diesel Spray Structure at Engine-Like Ambient Density, 21st Annual Conference on Liquid Atomization and Spray Systems, May 2008.*

Foley et al., Xenon Contrast Enhancement in Computed Body Tomography, (1978), <http://pubs.rsna.org/doi/abs/10.1148/129.1.219>.*

Lim et al., Measurement of Spatially Resolved Mean Velocities in a Transient Spray using Statistical Image Correlation Velocimetry, (2007), <http://scholar.google.com/citations?view_op=view_citation&hl=en&user=4D08jqgAAAAJ&citation_for_view=4D08jqgAAAAJ:_FxGoFyzp5QC>.*

Carlson, William D., "Three-dimensional imaging of earth and planetary materials", Aug. 23, 2006, pp. 133-147, Elsevier, available at www.sciencedirect.com.

Choi, Inyong, "Studies of Temperature Elevation Due to the Pre-flame Reaction in a Spark-ignition Engine with CARS Temperature Measurements Usign Fuels of Various Octane Numbers", May 7, 2001, pp. 719-724, JSME International Journal Series B, vol. 45, No. 3, 2002.

De Clerkc, Nora M., "High-Resolution X-ray Microtomography for the Detection of Lung Tumors in Living Mice", Feb. 11, 2004, pp. 374-379, Neoplasa vol. 6, No. 4, Jul. Aug. 2004.

Kawahara, Nobuyuki, "Unburned gas temperature measurement in a spark-ignition engine using fibre-optic heterodyne interferometry", Dec. 12, 2001, pp. 125-131, Institute of Physics Publishing Measurement Science and Technology 13 (2002).

Liu, Xin et al., "Development of ultrafast computed tomography of highly transient fuel sprays", downloaded from SPIE Digital Library on Nov. 16, 2009, pp. 21-28, SPIE vol. 5535, Bellingham, WA, 2004.

Lucht, Robert P., "Unbured Gas Temperatures in an Internal Combustion Engin"; May 4, 1987, pp. 41-61, Combust. Sci. and Tech, 1987, vol. 55, Gordon and Breach Science publishers, Inc., Great Britain.

Mitchell, J. B. A., "X-Ray Synchrotron Radiation Probing of an Ethylene Diffusion Flame", Jun. 10, 2002, pp. 308-315, Elsevier Science Inc., Combustion and Flame 131: 308-315 (2002).

Mitchell, J. B. A. "A new apparatus for the measurement of X-ray absorption by flame generated particles", Nuclear Instruments and Methods in Physics Research B 207 (2003) pp. 227-231, Elsevier Science, available at www.sciencedirect.com.

Sanders, S. T., "Gas Temperature Measurements During Ignition in an HCCI Engine", SAE Technical Paper Series 2003-01-0744, 2003 SAE World Congress, Detroit, Michigan, Mar. 3-6, 2003, SAE International, Warrendale, PA.

* cited by examiner

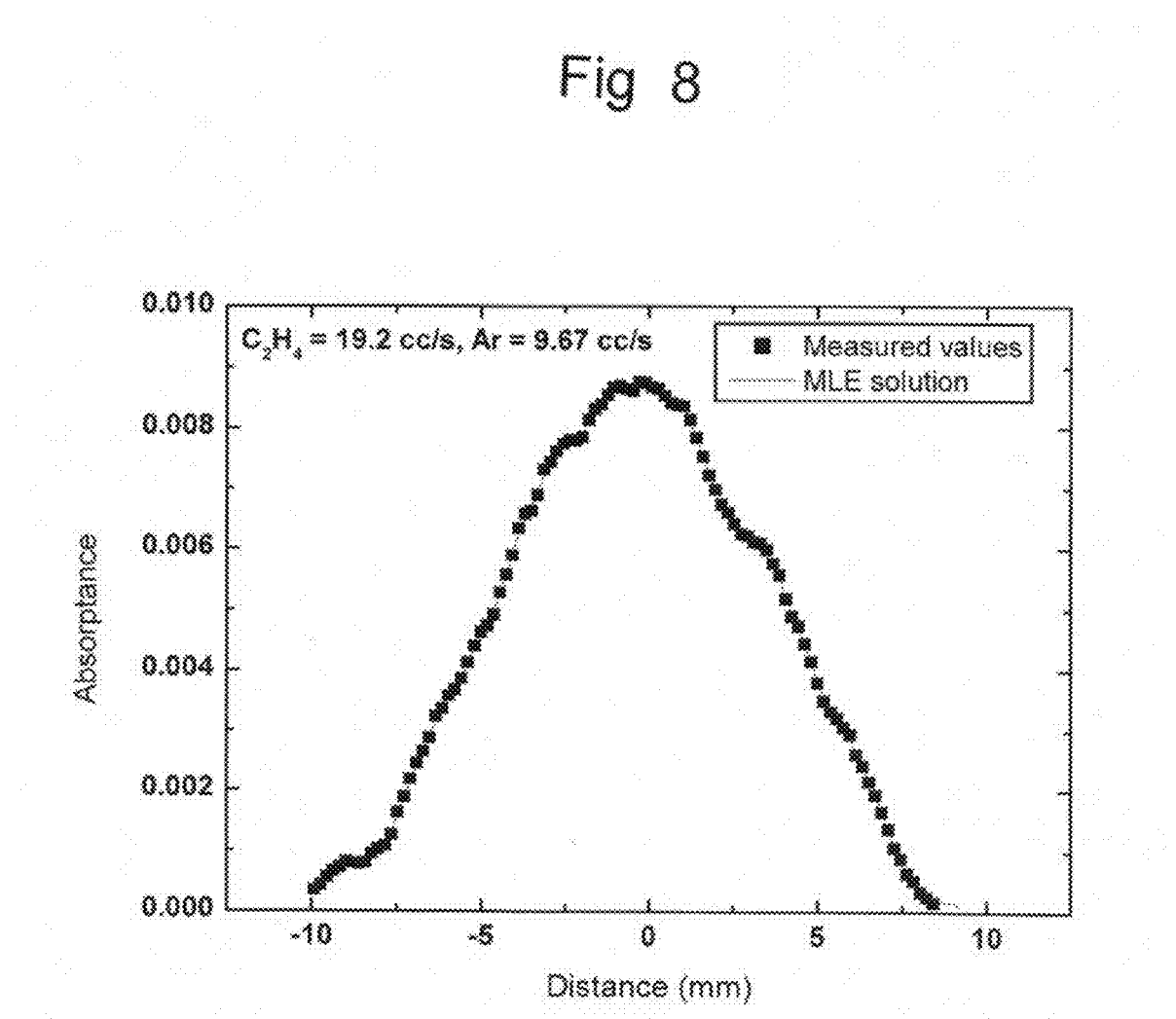

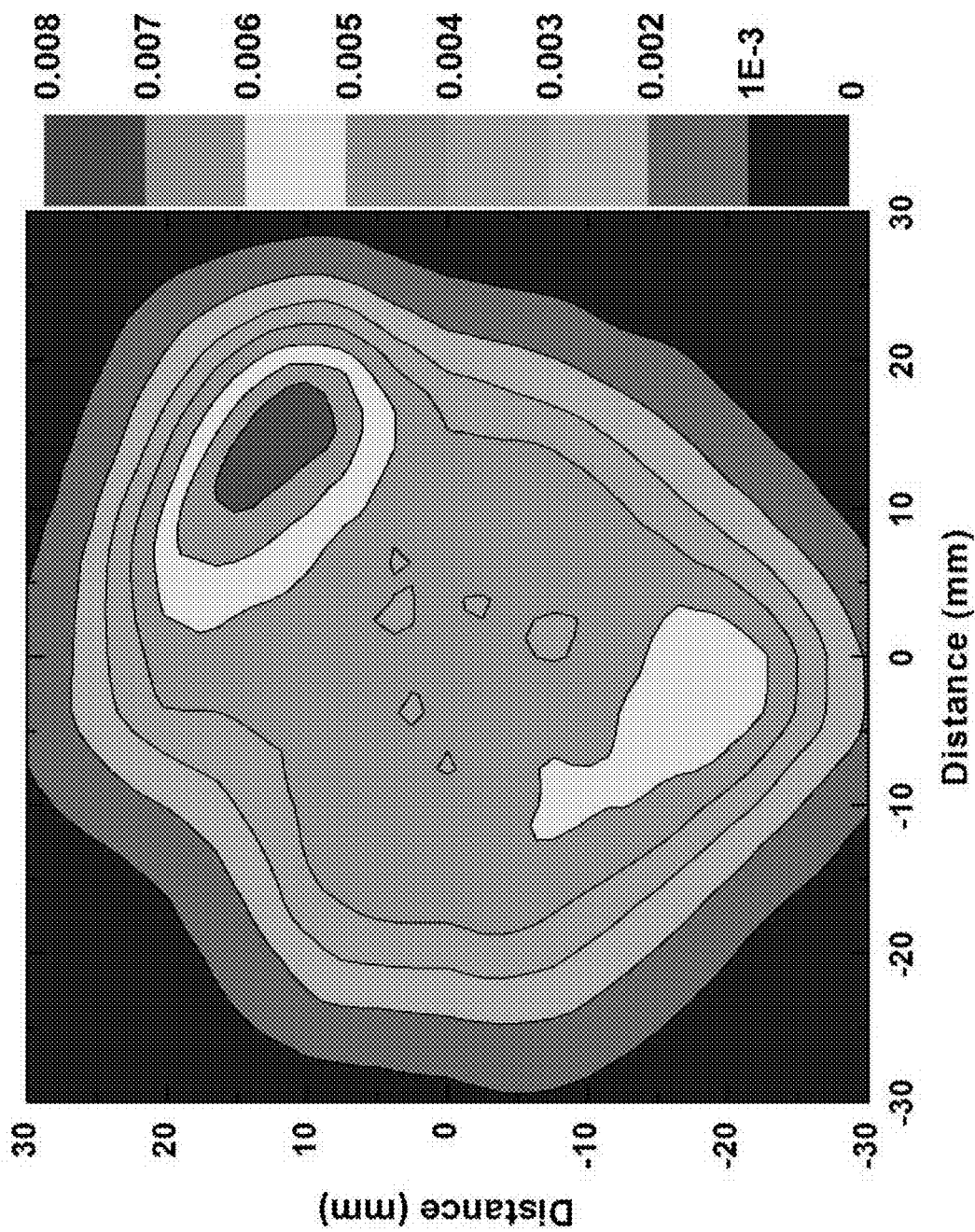

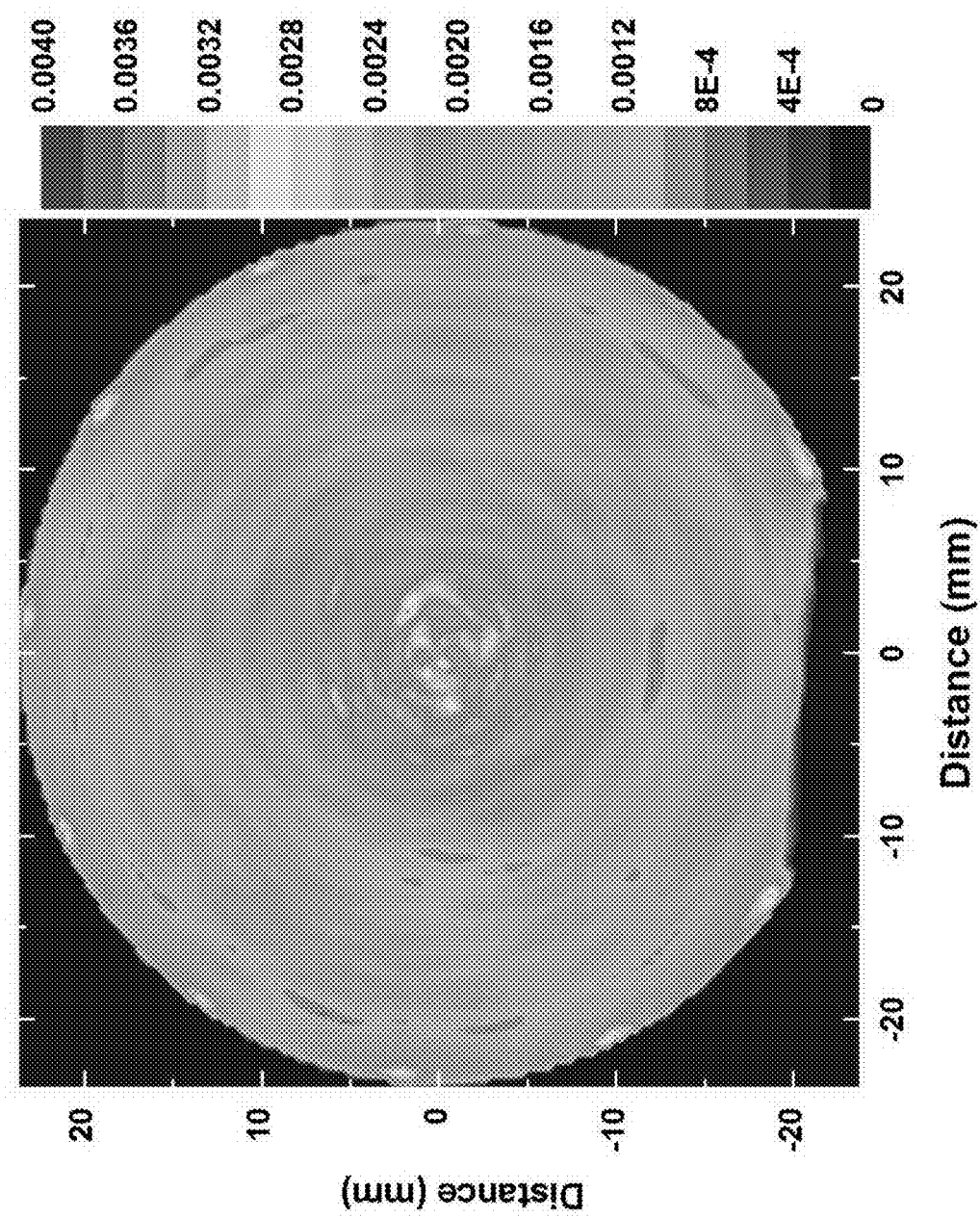

METHOD FOR CHARACTERIZING FLAME AND SPRAY STRUCTURES IN WINDOWLESS CHAMBERS

CROSS-REFERENCE TO RELATED APPLICATIONS

The present application is a continuation-in-part of application Ser. No. 12/561,739 filed Sep. 17, 2009, which in turn is related to and claims all available benefit of provisional application 61/142,505 filed Jan. 5, 2009.

BACKGROUND

The present disclosure is directed to tomography systems for sensing gas and particulate density distributions within an enclosure having no viewing aperture.

There is currently a wide range of diagnostic techniques that can be used to obtain detailed information from open flames or from combustors with optical access. However, in many industrial setting, combustors are not generally provided with optical access. Acoustic pyrometers have been used to measure flame structure inside boilers. However, acoustic pyrometers also require open access to the flame. For diagnostics within combustors, Tunable Diode Laser Absorption Spectroscopy (TDLAS), Coherent Anti-stokes Raman Spectroscopy (CARS), and Heterodyne Interferometry have been shown to be feasible in obtaining temperatures with some degree of accuracy. However, all these methods require optical access for measurements within a chamber. Therefore, an unfulfilled need exists for obtaining structural information about turbulent flames within windowless chambers, such as within internal combustion engines. A similar unfulfilled need exists for obtaining structural information about spray droplet location and density within drying towers for ensuring uniform application of cosmetic coatings. A similar unfulfilled need exists in tablet coaters used in the pharmaceutical industry for ensuring uniformity of functional coatings.

X-ray tomography is used in a wide range of applications, ranging from 3-dimensional imaging of earth and planetary materials to detecting lung tumors in living mice. Most of the convention applications of X-Ray tomography are for steady state or immobile objects. Recently, Lui et al. has demonstrated the utility of fast x-rays to obtain the near injector characteristics of turbulent sprays. Recently, X-Ray absorption has also been used in small laminar flames to obtain information on particulate formation. The present application is directed to the use of X-ray tomography to address the various unfulfilled needs identified above as well as other needs having similar physical structural restrictions. It is known that X-rays can penetrate through very dense materials such as concrete and metal and still detect density measurements that are less than 0.1%. In addition, utilizing background masking, internal structures within dense objects can be visualized.

Of particular interest is an analysis of flame structure within automotive engines. New federal regulations mandate much lower pollutant emissions from automotive engines than are currently permitted. The current technology is not suitable for diagnosing the flame structure under the high pressure and temperature that exists within an automotive engine using x-ray scanning tomography. Another area of particular interest involves obtaining pattern factors on blades inside turbines. Many newer turbine engines used for power production run at high temperatures that can significantly degrade thermal barrier coatings if hot spots exist. The present system is intended to use x-ray scanning tomography to enable manufacturers to obtain in situ, the pattern factor on turbine blades, leading to the potential for significant improvements in the design and operation of turbine engines.

SUMMARY

In one aspect, apparatus can be assembled for detecting variations in gas density within a volume surrounded by an entirely closed metal wall. The metal wall can be made of any material through which optical light cannot penetrate. The apparatus can include a source of x-rays positioned at a selected location outside the closed metal wall. A detector can be positioned outside the closed metal wall at a location suitable to detect x-rays from the source passing entirely through a portion of the volume surrounded by the closed metal wall. The detector can have a plurality of sensors arranged in at least one row to capture a dimensionally distributed view of detected x-rays. The detector can have an output providing data reflecting that dimensionally distributed view. A processor can be coupled to the output of the detector to analyze the data. A display can be coupled to the processor to show results of the processor analysis. The results can be graphical or pictorial in presentation.

The closed metal wall can define a housing for a flame, spray or other gaseous distribution. The housing can be mounted on a rotating platform to permit the generation of multiple views of the same housing and contents from different angles. The entirety of the apparatus, excluding the display, can be located with a radiation shield, made of lead or other suitable material to prevent any stray output of x-rays. The X-Ray source can be tuned to different frequencies (or strength in terms of KeV) so that differential absorption by the combustor wall material and the gases inside is optimized. Alternatively, the detectors can be tuned to look at these specific frequencies using filters.

The source of x-rays can be a single source having an angularly distributed output sufficient to penetrate at least a plane across the entirety of the volume surrounded by the closed metal wall. A detector suitable for use with such a single source can be a linear array aligned in the plane of the angularly distributed output. Alternatively, the source of x-rays can be a plurality of sources spaced around the outside of the closed metal wall. Where a plurality of sources is employed, each source can be focused so that the emitted radiation traverses only a selected portion of the volume surrounded by the closed metal wall. Where a plurality of sources is employed, the detector can take the form of a like plurality of detectors, with each detector aligned to receive x-rays from at least one of the plurality sources. The detectors generally can be either linear arrays or two-dimensional arrays of sensors. Where a plurality of sources is employed, a rotating platform is generally not employed. A collimator or filter can be positioned between any source of x-rays and the closed metal wall to focus and select the x-rays to impinge on all or only a portion of the volume surrounded by the closed metal wall.

The processor can be a general purpose computer programmed to process the data output from the detector(s) to correct for any beam hardening of the x-rays as they pass through the closed metal wall. The processor can also be programmed to apply the Maximum Likelihood Estimation method to the data output from the detector(s) to generate on the display a reconstructed image of the gas density in at least one plane of the volume surrounded by the closed metal wall. Inverse Radon Transforms can also be used for deconvolution. The processor can be programmed to apply the method to data collected over a period of time to generate converging statistics concerning the gas flow within the volume surrounded by the closed metal wall. The path integrated reconstruction generated by such a processor can measure even small differences in gas density using soft x-rays, particularly if the gas is doped with an absorbing agent that will interact with the penetrating x-rays. Where a plurality of sources and detectors is employed, the processor can be programmed to apply the method to the data output from each of the detectors to generate a plurality of simultaneous images, which can be combined to show an enhanced reconstructed image of the gas density in at least one plane of the volume surrounded by the closed metal wall.

In another aspect, a method is provided for detecting variations in particulate distribution within a volume surrounded by a closed metal wall through which optical light cannot penetrate. The method can include positioning a source of x-rays at a selected location outside the closed metal wall, and positioning a detector outside the closed metal wall at a location suitable to detect x-rays from the source passing entirely through a portion of the volume surrounded by the closed metal wall. The method can include supplying a detector having a plurality of sensors arranged in at least one row to capture a dimensionally distributed view of detected x-rays, the detector having an output providing data reflecting that dimensionally distributed view. The method also includes coupling a processor to the output of the detector to analyze the data. The method used by the processor can include processing the data to correct for any beam hardening of the x-rays as they pass through the closed metal wall, to apply the Maximum Likelihood Estimation method to generate on the display a reconstructed image of the gas density, and to use Inverse Radon Transforms for deconvolution. The method can include coupling a display to the processor to show results of the processor analysis. The results can be graphical or pictorial in presentation.

One feature of the present method is the ability to measure conditions within an enclosed metal volume that are relevant to combustion that may enable stricter quality control and reduced pollution emission.

Another feature of the present method is the ability to measure conditions within an enclosed metal volume that are relevant to decorative and functional coating processes that may lead to enhanced control of drug delivery.

Another feature of the present method is the ability to measure conditions within an enclosed metal volume that are relevant to the degradation of barrier coatings in high temperature conditions that may lead to significant improvements in the design and operation of turbine engines.

Other features of the present apparatus and methods, along with the corresponding advantages of those features, will become apparent from the following discussion of the following preferred embodiments exemplifying the best mode of practice, which is illustrated in the accompanying drawings. The components in the figures are not necessarily to scale, emphasis instead being placed upon illustrating the principles of the features. Moreover, in the figures, like referenced numerals designate corresponding parts throughout the different views.

BRIEF DESCRIPTION OF THE DRAWINGS

FIG. 8 is a graph of the path integrated absorptances measured in the ethylene/argon flame in Example I as compared to the MLE solution

FIG. 12b is a color presentation of the local surface area density in the same plane of the water spray in Example II measured using an optical patternator.

FIG. 13a is a color presentation of the RMS of local mass concentrations in a plane of the water spray in Example II measured by the system 10.

DESCRIPTION OF PREFERRED EMBODIMENTS

Figure 1:
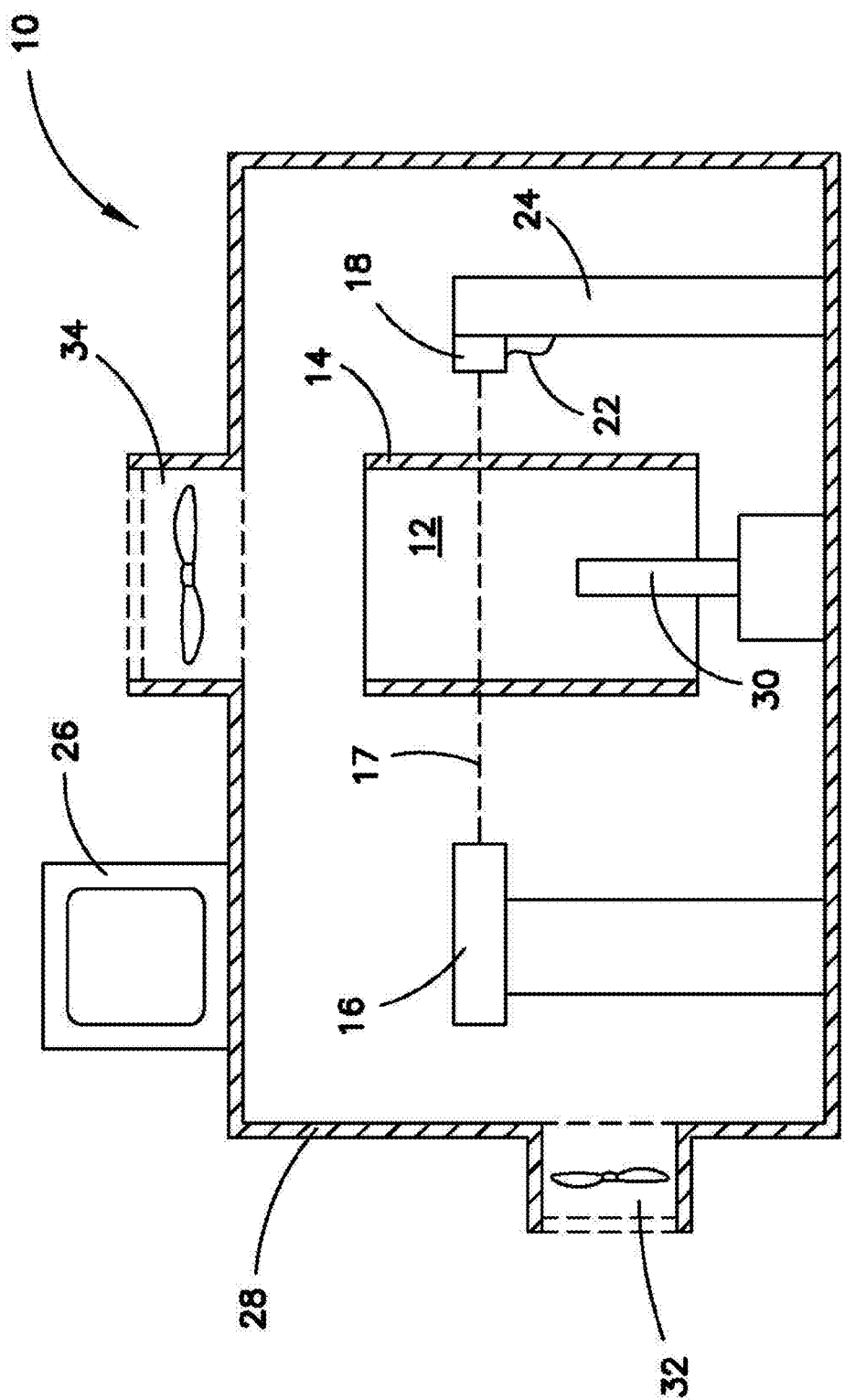
FIG. 1 is a schematic side elevation view of an apparatus for detecting variations in gas density within a volume surrounded by a closed metal wall.

An apparatus 10 is shown schematically in FIG. 1 for detecting variations in gas density within a volume 12 surrounded by a closed metal wall 14. A source of x-rays 16 is positioned at a selected location outside the closed metal wall 14 so that the x-rays are directed toward the volume 12. A detector 18 is positioned outside the closed metal wall 14 at a location suitable to detect x-rays from the source 16 passing entirely through at least a portion of the volume 12. The detector 18 can have a plurality of sensors 20 arranged in at least one row, as shown schematically in FIG. 2, to capture a dimensionally distributed view of the detected x-rays. The detector 18 can have an output 22 providing data reflecting that dimensionally distributed view. A processor 24 can be coupled to the output 22 of the detector 18 to analyze the data. A display 26 can be coupled to the processor 24 to show results of the processor analysis. The results can be graphical or pictorial in presentation. The entirety of the apparatus 10, excluding the display 26, can be located with a radiation shield 28, made of lead or other suitable material to prevent any stray output of x-rays.

The closed metal wall 14 can define a housing for a flame or other gaseous distribution. The closed metal wall 14 can be positioned to surround a source 30 of combustible gas or other gas under study. The source of gas 30 can be connected to exterior supply lines for supplying a variety of gases. The radiation shield 28 can include a gas input 32 for providing a measured amount of oxygen-containing gas for mixture with the combustible gas. The oxygen-containing gas can simply be ambient air or a specially formulated gas. An exhaust outlet 34 can be provided in the radiation shield 28 to provide for a controlled exhaustion of the combustion products and other gases from within the radiation shield 28. The gas input 32 and the exhaust outlet 34 desirably can be controlled so that analysis of the combustion or other gaseous distribution within the closed metal wall 14 can occur over a variety of pressures.

Figure 2:
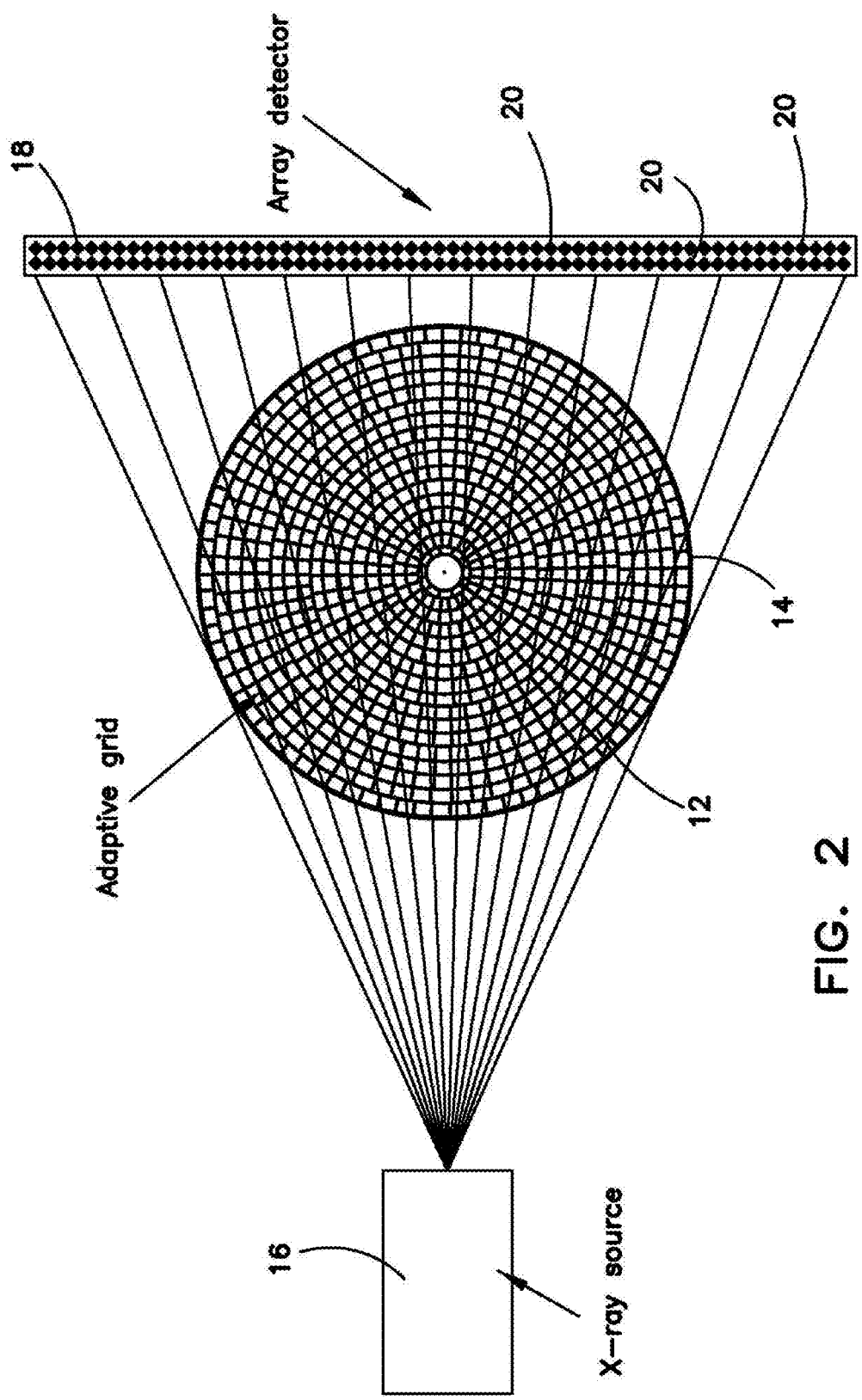
FIG. 2 is a schematic plan view of elements of the apparatus shown in FIG. 1, also showing an adaptive grid used to compute the local extinction coefficients.

The source of x-rays 16 can be any convenient source having a beam angle sufficient to cover the selected portion of the area 12. The X-Ray source 16 can be tuned to different frequencies (or strength in terms of KeV), preferably over a range of between 1 KeV and 100 KeV, so that the differential absorption by the closed metal wall 14 and the gases inside volume 12 is optimized. A suitable source is available from Hamamatsu Photonics K.K., Hamamatsu, Japan such as Model A10220-20. As shown in FIG. 2, the beam angle of the x-ray source 16 is sufficient to cover at least laterally the whole of the volume 12 within the closed metal wall 14. The detector 18 can be any convenient x-ray responsive camera having a width sufficient to capture the x-rays passing through the selected portion of the volume 12. The detector is desirably tuned or filtered to receive only a selected x-ray frequency in the range of between 1 KeV and 100 KeV.

As shown in FIG. 2, the array detector 18 extends over a linear distance sufficient to capture the x-rays passing through the lateral whole of the volume 12 within the closed metal wall 14. The detector 18 can have a linear array or a two dimensional array of sensors 20. When only a linear array is employed, the detector 18 captures the x-rays in a single plane 17 defined by the linear array of the detector 18 and the point of origin of the x-ray source 16. A suitable linear array detector is available from Hamamatsu Photonics K.K., Hamamatsu, Japan such as Model C9750-10TC. The processor 24 can be any general purpose computer programmed to capture and analyze the data output from the detector 18. FIG. 2 additionally shows a planar portion of the volume 12 divided into an adaptive grid used to obtain the local extinction coefficients in a manner similar to that disclosed in our prior publication "Optical Patternation of a Multi-hole Fuel Spray Nozzle," appearing in Atomization and Sprays, vol. 15, pp. 687-698. The major advantage of the grid is that all the local information is obtained on areas that are very equal to each other, providing for uniform spatial resolution of the measurements. The specific programs and analysis are discussed below in connection with the operative examples.

Figure 3:
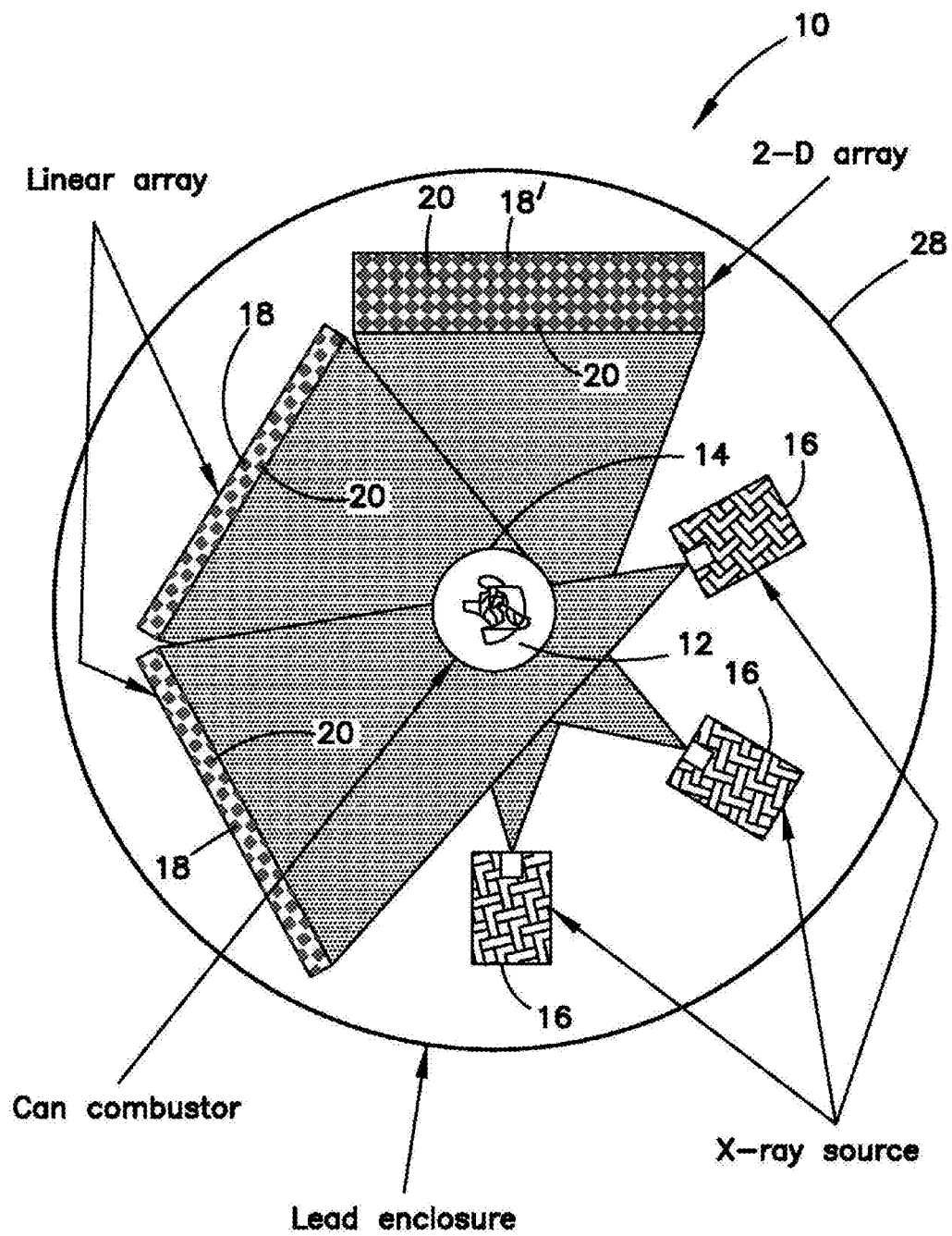
FIG. 3 is a schematic plan view of another apparatus for detecting variations in gas density within a volume surrounded by a closed metal wall using a plurality of sources and detectors, one of the detectors being a two-dimensional array.

FIG. 3 is a schematic plan view of another apparatus 10 for detecting variations in gas density within a volume 12 surrounded by a closed metal wall 14 using a plurality of x-ray sources 16 and a plurality of detectors 18 and 18'. While two of the detectors 18 have a linear array of sensors 20, one of the detectors 18' has a two dimensional array of sensors 20 so that more than a single plane of the volume 12 can be analyzed. The arrays of sensors 20 in the detectors 18 and 18' capture a dimensionally distributed view of the detected x-rays. Each of the detectors 18, 18' can have an output providing data reflecting that dimensionally distributed view to a processor 24 (not shown in FIG. 3) to analyze the data. As in the apparatus shown in FIG. 1, a display 26 can be coupled to the processor 24 to show results of the processor analysis. The entirety of the apparatus 10, excluding the display 26, can be located with a radiation shield 28, made of lead or other suitable material to prevent any stray output of x-rays.

The system 10 shown in FIG. 3 can be used to measure the extinction caused by a flame or a spray inside the closed metal wall 14 from three view angles and 1280 parallel lines per view angle. The system 10 shown in FIG. 3 can provide a spatial resolution of approximately 3500 points in the plane of measurement. Therefore, for a typical 75 mm diameter internal combustion engine cylinder, the spatial resolution obtained is approximately 1.2 $mm^2$, which is sufficient for most industrial and research applications. The speed at which these measurements can be obtained is 1000 Hz. The detector 18' can have a 2-dimensional array of 1280×16 sensors 20. This detector 18' can be used to obtain multi-planar extinction images at a framing rate of 1000 Hz. The images obtained by detector 18' can be used to simultaneously obtain velocity information from axi-symmetric turbulent sprays and flames.

Figure 4:
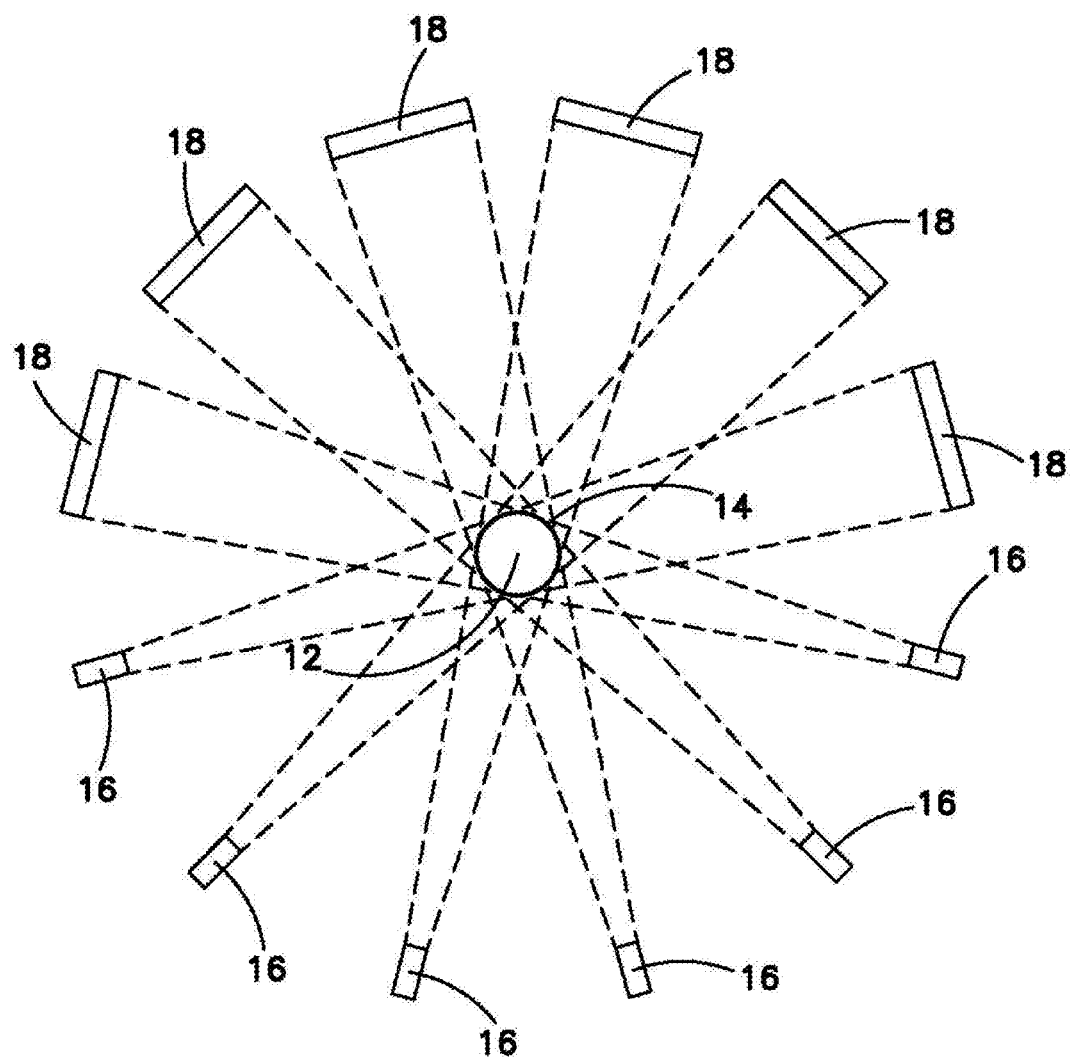
FIG. 4 is a schematic plan view of yet another apparatus for detecting variations in gas density within a volume surrounded by a closed metal wall using a plurality of sources and detectors.

FIG. 4 is a schematic plan view of yet another apparatus 10 for detecting variations in gas density within a volume 12 surrounded by a closed metal wall 14 using a plurality of x-ray sources 16 and a plurality of detectors 18. Any of the detectors 18 can have either a linear array of sensors or a two dimensional array of sensors so that more than a single plane of the volume 12 can be analyzed. The arrays of sensors in the detectors 18 capture a dimensionally distributed view of the detected x-rays. Each of the detectors 18 can have an output providing data reflecting that dimensionally distributed view to a processor 24 (not shown in FIG. 4) to analyze the data. As in the apparatus shown in FIG. 1, a display 26 can be coupled to the processor 24 to show results of the processor analysis. The entirety of the apparatus 10, excluding the display 26, can be located with a radiation shield 28 (not shown in FIG. 4), made of lead or other suitable material to prevent any stray output of x-rays.

Figure 5:
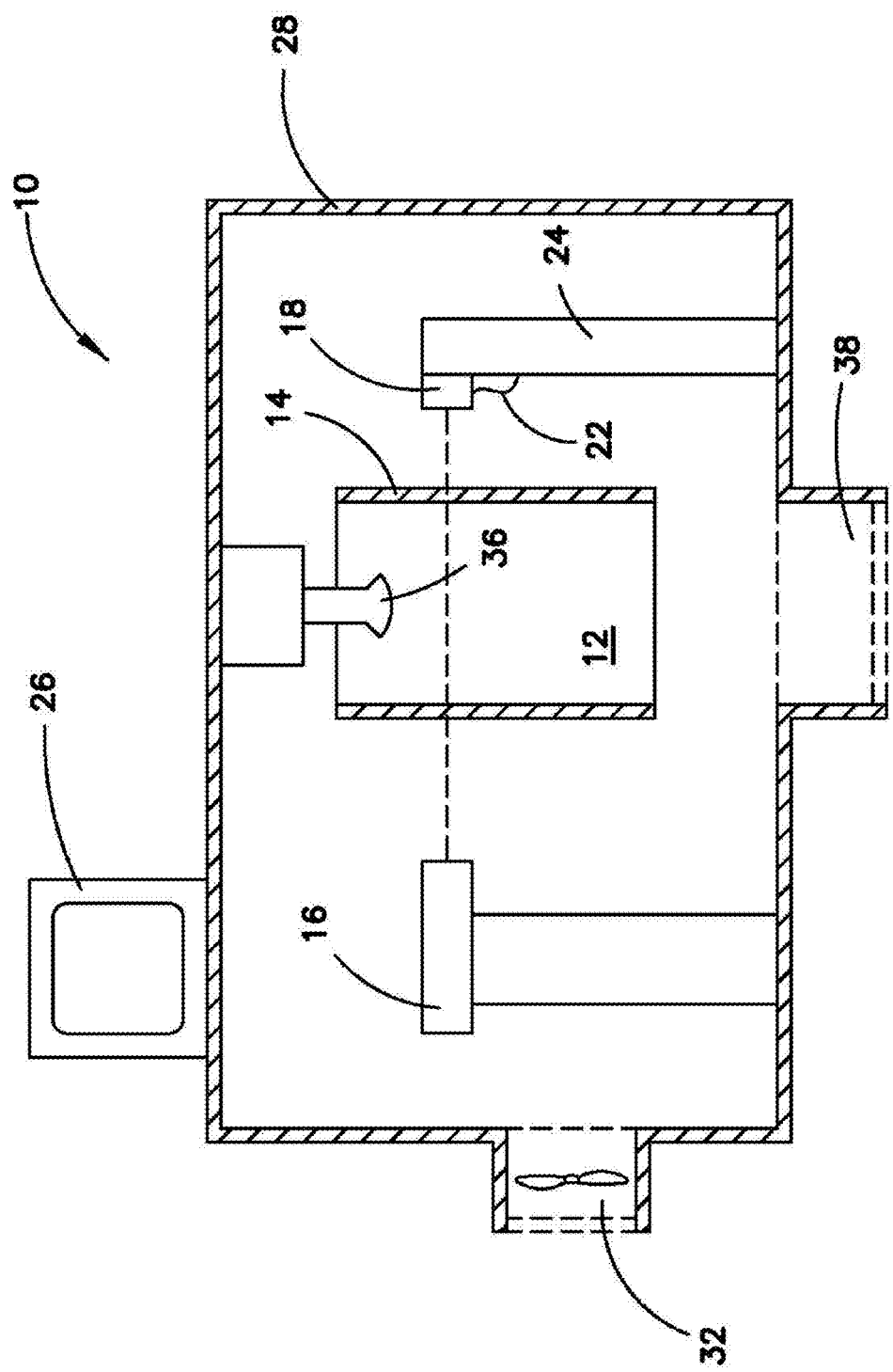
FIG. 5 is a schematic side elevation view of an apparatus for detecting variations in spray density within a volume surrounded by a closed metal wall.

Another apparatus 10 is shown schematically in FIG. 5 for detecting variations in spray density within a volume 12 surrounded by a closed metal wall 14. A source of x-rays 16 is positioned at a selected location outside the closed metal wall 14 so that the x-rays are directed toward the volume 12. A detector 18 is positioned outside the closed metal wall 14 at a location suitable to detect x-rays from the source 16 passing entirely through at least a portion of the volume 12. The closed metal wall 14 can define a housing for a spray head 36 that can be coupled to a source of liquid that is atomized or otherwise divided into an aerosol for distribution within the volume 12. The spray head 36 can be connected to exterior supply lines for supplying a variety of liquids. A drain outlet 38 can be provided in the floor of the radiation shield 28 to allow for an outflow of any residue from the spray head 36. The gas input 32 and the drain outlet 38 desirably can be controlled so that analysis of the aerosol process occurring within the closed metal wall 14 can occur over a variety of pressures.

The detector 18 shown in FIG. 5 can have a plurality of sensors 20 arranged in at least one row, as shown schematically in FIG. 2, to capture a dimensionally distributed view of the detected x-rays. The detector 18 can have an output 22 providing data reflecting that dimensionally distributed view. A processor 24 can be coupled to the output 22 of the detector 18 to analyze the data. While only a single source 16 and detector 18 are illustrated in FIG. 5, it will be appreciated that it is preferable that a plurality of sources 16 and detectors 18 be provided. The plurality of sources 16 and detectors 18 can be arranged as shown in FIG. 3 or 4, or arranged in any other fashion suitable for the desired investigation. A display 26 can be coupled to the processor 24 to show results of the processor analysis. The entirety of the apparatus 10, excluding the display 26, can be located with a radiation shield 28, made of lead or other suitable material to prevent any stray output of x-rays.

Figure 6:
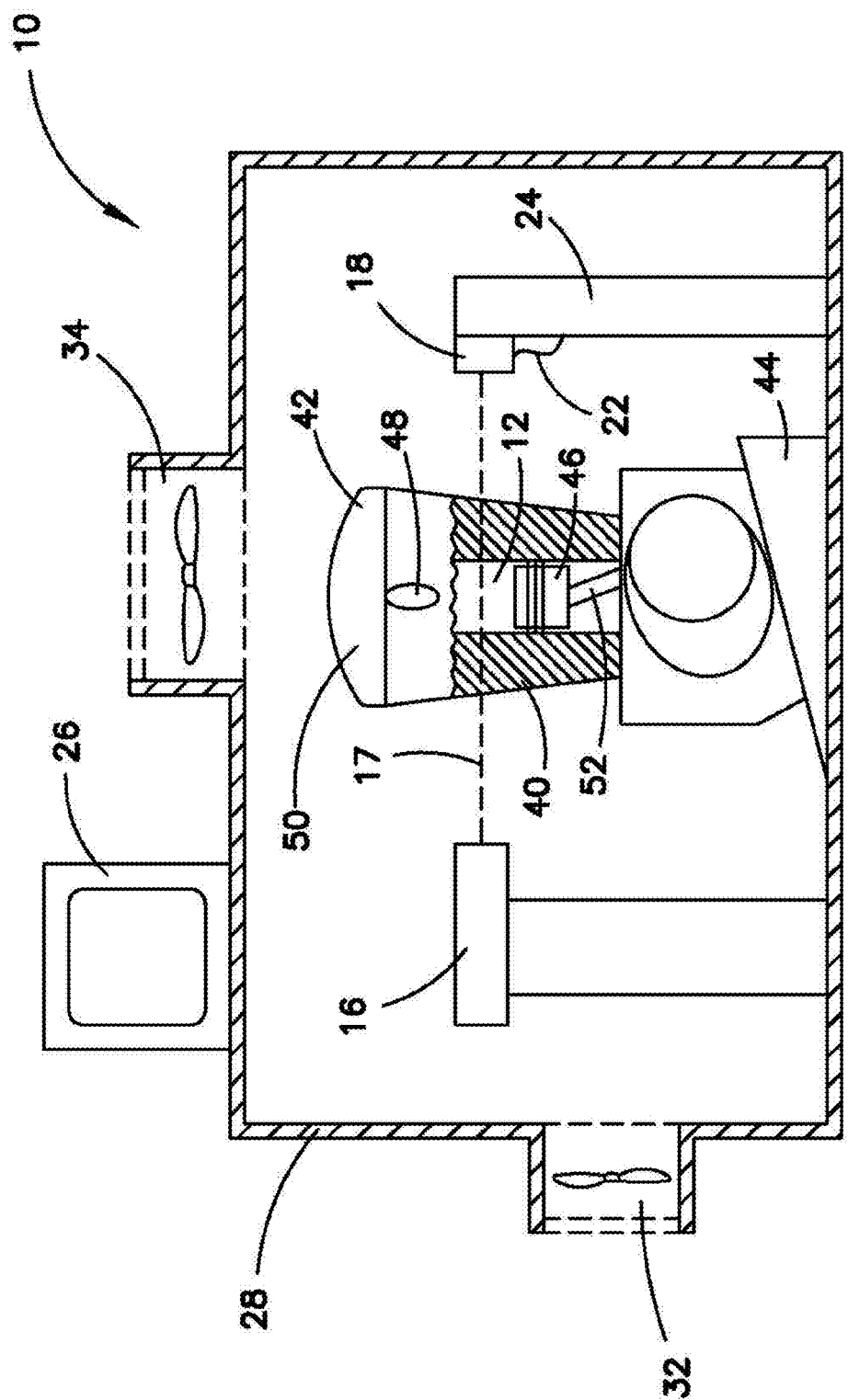
FIG. 6 is a schematic side elevation view of an apparatus for detecting variations in gas density within a volume defined by the cylinder wall of a single cylinder engine.

Yet another apparatus 10 is shown schematically in FIG. 6 for detecting variations in gas density within a volume 12 defined by the cylinder wall 40 of an engine 42. The engine 42 can be suitably mounted on a base 44 so that the cylinder wall 40 is arranged generally perpendicular to the plane 17 of x-rays emitted by the source 16 and detected by detector 18. The engine 42 is situated on the base 44 so that the volume 12 being analyzed is above the highest position of the vertically reciprocating piston 46 within the cylinder wall 40. The detector 18 is positioned at a location suitable to detect the x-rays from the source 16 passing entirely through at least a portion of the volume 12 defining the combustion chamber of the engine 42. While FIG. 6 shows only a single cylinder engine 42, it will be appreciated that multi-cylinder engines could be suitably position within a radiation shield 28 in the same manner. The engine 42 can include a spark plug 48, head 50, piston rod 52, and other conventional elements of an internal combustion engine, which need not be illustrated in detail. The gas input 32 and the exhaust outlet 34 desirably can be controlled so that analysis of the combustion process occurring within the engine 42 can be studied over a variety of conditions.

The detector 18 shown in FIG. 6 can have a plurality of sensors 20 arranged in at least one row, as shown schematically in FIG. 2, to capture a dimensionally distributed view of the detected x-rays. The detector 18 can have an output 22 providing data reflecting that dimensionally distributed view. A processor 24 can be coupled to the output 22 of the detector 18 to analyze the data. A display 26 can be coupled to the processor 24 to show results of the processor analysis. The entirety of the apparatus 10, excluding the display 26, can be located with a radiation shield 28, made of lead or other suitable material to prevent any stray output of x-rays. While only a single source 16 and detector 18 are illustrated in FIG. 6, it will be appreciated that it is preferable that a plurality of sources 16 and detectors 18 be provided. The plurality of sources 16 and detectors 18 can be arranged as shown in FIG. 3 or 4, or arranged in any other fashion suitable for the desired investigation.

While a number of illustrated examples of suitable apparatus 10 have been presented, it will be appreciated that additional arrangements could be constructed using the same basic principles. The system can use various computational methods to extract the desired information from the data provided to the processor 24. A particularly desirable method obtains the local extinction information from the path integrated measurements using the Maximum Likelihood Estimation (MLE) method developed by Vardi, Y., and Lee, D., in their article entitled "From Image Deblurring to Optimal Investments: Maximum Likelihood Solutions for Positive Linear Inverse Problems," *J. Statist. Soc. B*, vol. 55, p. 569, 1993. The MLE method converges to the optimal solution (see: Vardi and Lee, 1993) and forms the basis for the three axis system of FIG. 3 and the six axis system of FIG. 4 as well. The local extinction coefficients are obtained based on an adaptive grid as shown in FIG. 2 that is similar to that used in the optical patternator as explained in the article of Lim, J., and Sivathanu, Y., entitled "Optical Patternation of a Multi-hole Fuel Spray Nozzle," Atomization and Sprays, vol. 15, pp. 687-698, 2005. The major advantage of the grid is that all the local information is obtained on areas that are very equal to each other, providing for uniform spatial resolution of the measurements. All the areas of the grid shown in FIG. 2 are roughly of equal size, except the very middle area, which is approximately three times larger. This is deliberately chosen so that the solution in the center, which is always has the lowest SNR, is averaged over a slightly larger area. Only a single axis is shown in FIG. 2, but additional axes are desirable.

The processor 24 can additionally be programmed to correct for any beam hardening of the x-rays as they pass through the closed metal wall 14. This correction is achieved by initially looking at the data provided to the processor when the volume 12 is filled with a calibration gas that has a known absorption coefficient for of x-rays, such as Argon or Xenon. The anticipated absorption for these gases are available from an NIST database located at http//www.nist.gov/pml/data/xraycoef/index.cfm. However, since the X-Ray has been hardened to an unknown extent due to the passage of the beam through the metal wall 14, this value will be different. The specific absorption coefficient for the metal wall 14 can be calculated from the measured extinction using the calibration gas, and the wavelength of the X-Ray based on the information available in the NIST database. Essentially, this calibrates the wavelength of the X-Ray that has gone through the metal chamber given a known wavelength input from the source. This procedure can be repeated for different values of input X-Ray wavelength or energy level, and a look up table can be constructed for use by the processor 24 that shows the true X-Ray wavelength that is absorbed by the metal wall 14 defining the chamber. The same metal chamber can then be caused to contain a test gas, flame, spray, etc., for which X-Ray tomographic information is desired, and the processor 24 can make a suitable correction so that the display 26 reflects a true picture within the closed metal wall 14. The methods discussed above are further detailed in the following working examples.

WORKING EXAMPLES

Example I

The apparatus shown in FIG. 1 was constructed to include a soft X-Ray source 16 (Hamamatsu Corporation, Model No. A10220-20) used to generate a 60° source output angle. A linear array detector 18 (Hamamatsu Corporation, Model No. C9750-10TC) was used to read the X-ray intensity. A metal combustor 14 was placed in the path of the x-rays, close to the linear array detector 18, to surround a source 30 of combustible gas. The gas consisted of a mixture of ethylene and argon issuing from a round nozzle, 15 mm in diameter. The path-integrated absorption of the x-ray intensity was measured using the linear array detector 18 at 1000 Hz. The absorption is observed to be entirely due to the local concentration of argon, and not from density variation in the flow. This was verified by igniting a corresponding flame without the argon dilution. The absorption observed with the flame without any argon dilution was negligible. The measurements were obtained for a total of 10 seconds (10000 data points) so as to obtain converged statistics of the turbulent flow. The measurements were deconvoluted to provide the mean and RMS of local absorptances using the Maximum Likelihood Estimation (MLE) method discussed above. Additional numerous references are available in the literature and therefore the details of the MLE method are not believed to be necessary here.

For the initial deconvolution, it is assumed that the steady state statistics of the turbulent flow (mean and RMS) issuing from a round burner is axi-symmetric. This assumption is appropriate for the mean and RMS (time averaged quantities) of turbulent flows from round tubes and jets even though the instantaneous flow may be non-axisymmetric. An assessment of the symmetric character of the flow can be obtained by either rotating the source 30 to a variety of positions while taking the same observations, or by simultaneously taking observations from a variety of positions using an apparatus 10 having a plurality of sources x-ray 16 such as are shown, for example, in FIG. 3 or 4. At the end of the deconvolution procedure, the local absorptances are available throughout an entire plane within the metal combustor wall 14. The density is sufficient for many quality assurance programs that are utilized in industry.

The local asborptances are converted to temperature and gas concentrations. This is achieved by using a state relationship approach developed by Bilger, R. W., in the article, "Reaction Rates in Diffusion Flames," appearing in *Combust. Flame*, vol. 30, pp. 277-284, 1977. The argon that enters the fuel tube is a passive scalar. Therefore, using the same methodology as disclosed by Sivathanu, Y. R., and Faeth, G. M., in the article "State Relationships for Major Gas Species in Non-premixed Hydrocarbon/Air Flames", appearing in *Combust. Flame*, vol. 82, pp. 211-230, 1990, the molar balance for the flame with 'a' moles of ethylene and 'b' moles of argon can be written as:

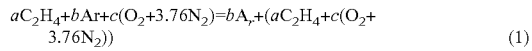

$$aC_2H_4 + bAr + c(O_2 + 3.76N_2) = bA_r + (aC_2H_4 + c(O_2 + 3.76N_2)) \quad (1)$$

Figure 7:
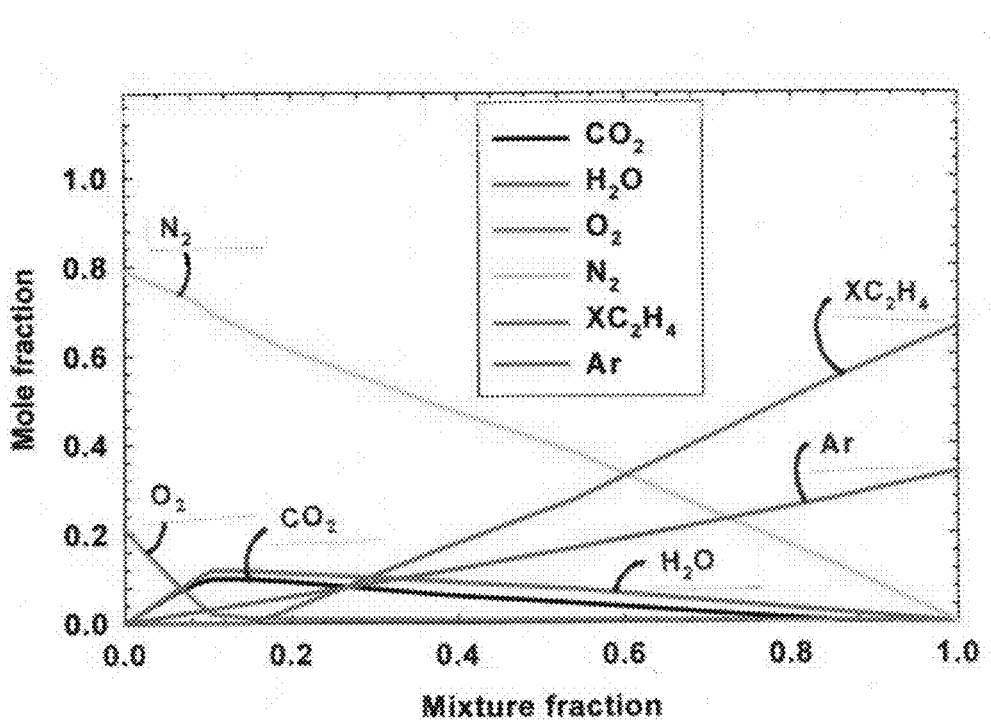
FIG. 7 is a graph of the state relationship for the ethylene/argon mixture used in Example I.

The different values of a and c can be obtained directly from standard ethylene state relationships. The tabular form of the ethylene state relationship is provided by the Sivathanu and Faeth (1990) article identified above. Since the input flow rates of a and b are known, the entire state relationship for the mixture can be easily constructed using Eq. (1). The state relationships thus obtained for the ethylene/argon flame are shown in FIG. 7. Using the state relationships, the concentrations of all the local species can be obtained if the mixture fraction is known. A direct computation using the heat of combustion of ethylene and equation of state for all gases provides the local temperature as well. The local mixture fraction is directly proportional to the local absorptances obtained from the deconvolution procedure.

The first experiment conducted used a mixture of ethylene and argon as the fuel. The burner diameter was 15 mm. The flow rate of ethylene was 19.2 cc/second and that of argon was 9.6 cc/second. Additional conditions with different flow rates in the same burner as well as different burner diameters were used. For all the conditions, the results obtained are similar. The path integrated absorptances obtained from the system 10 is shown in FIG. 8. The path integrated absorptances were deconvoluted using the MLE method to provide the local absorptances. The excellent convergence of the MLE algorithm to the measured values is also shown in FIG. 8. The absorptances provide the local argon concentrations, and are directly proportional to the local mixture fraction.

Figure 9A:
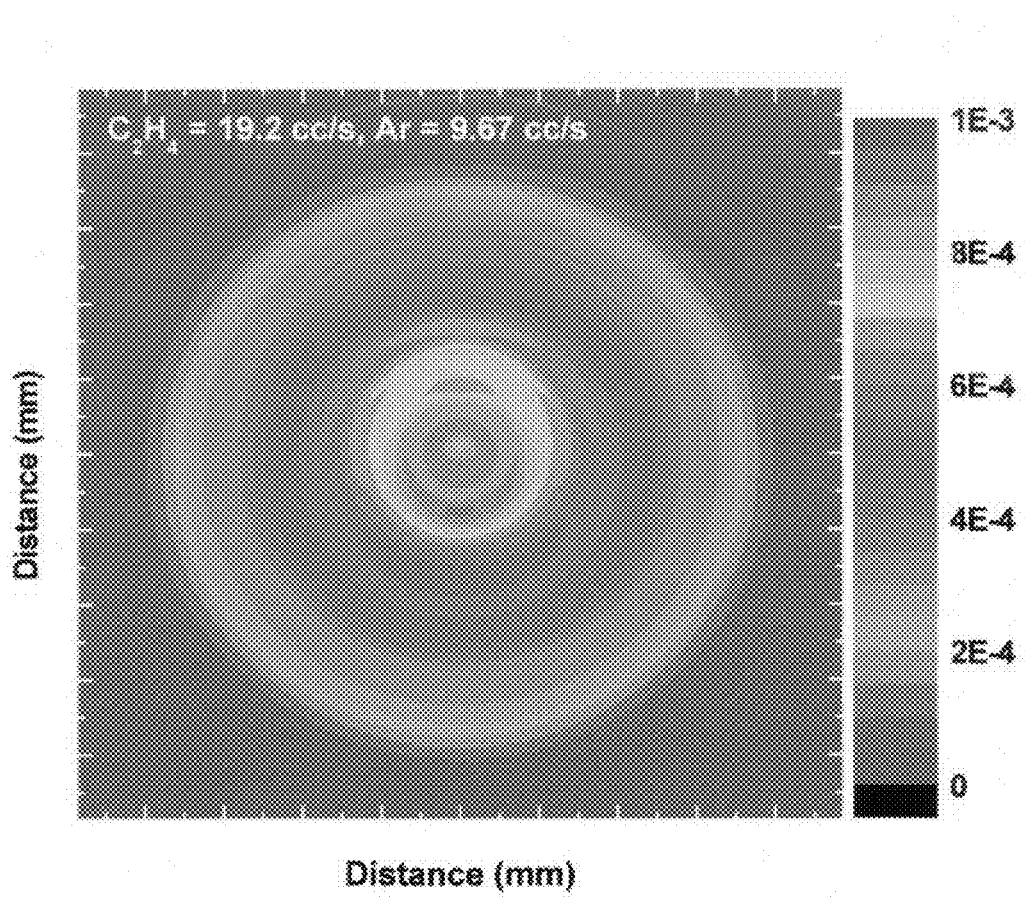
FIG. 9a is a color presentation of the local mean absorptances measured in the ethylene/argon flame in Example I.
Figure 9B:
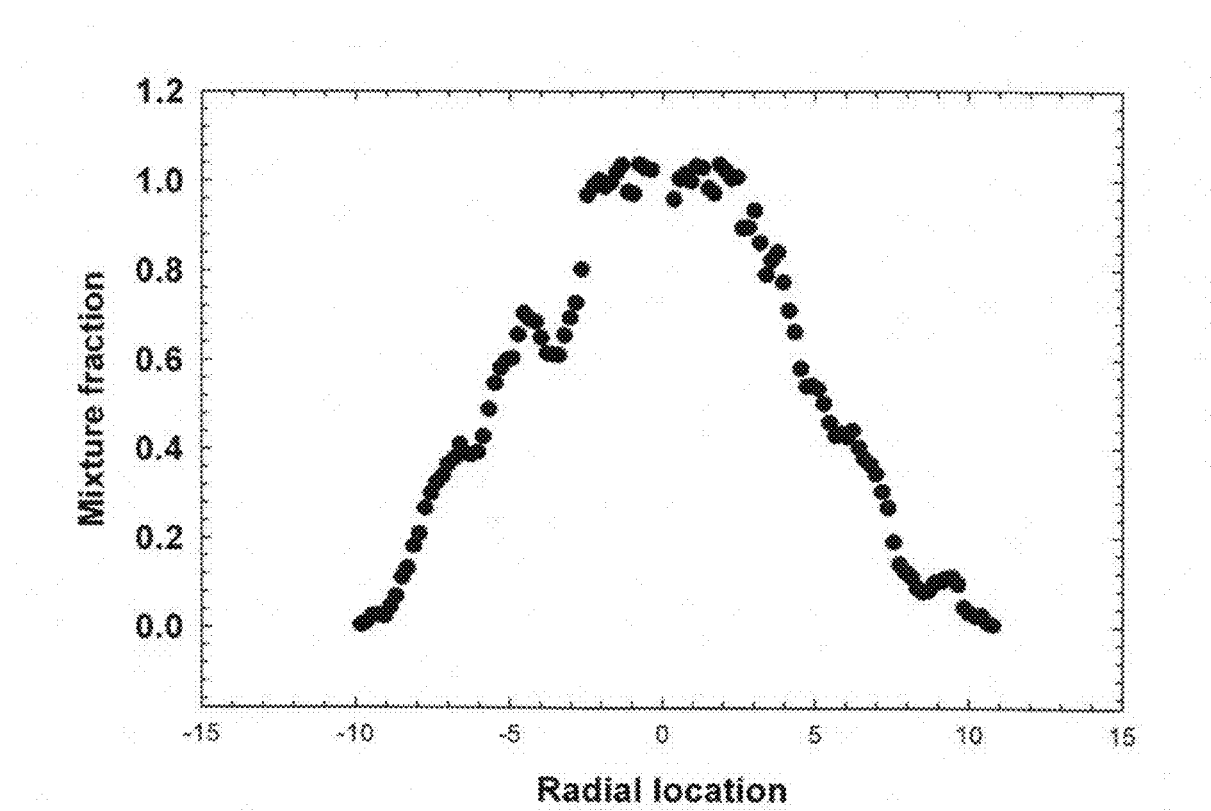
FIG. 9b is a graph of the radial profile of mixture fraction across the ethylene/argon flame in Example I.

The local mean absorptances and the mixture fraction obtained from the measurements (from a burner of 15 mm diameter) are shown in FIGS. 9a and 9b, respectively. Since only one view angle is available with the apparatus 10 shown in FIGS. 1 and 2, the angular resolution of the measurements is restricted to 180°. For turbulent flames issuing from a round nozzle, this is sufficient since all the moments (mean, RMS, etc.) are expected to be axisymmetric. The small asymmetry apparent in FIGS. 9a and 9b was captured accurately by the system 10, and is probably caused by an ignitor wire positioned near the exit of the nozzle 30.

Figure 10:
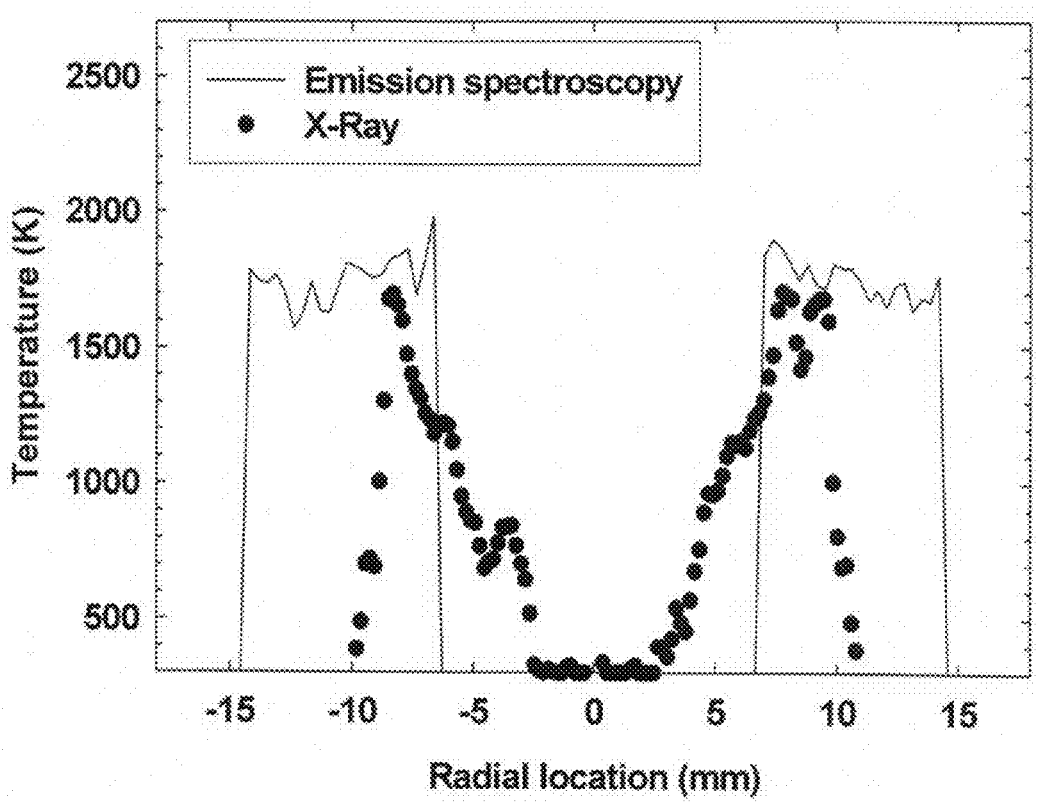
FIG. 10 is a graph of the radial profile of the local mean temperature across one plane of the ethylene/argon flame in Example I measured using the present x-ray system in comparison to that measured using emission spectroscopy.

For validation purposes, the metal combustor 14 of the system 10 shown in FIG. 1 was removed and temperature data was obtained from the same flame using an imaging spectrometer and emission tomography using the procedures set forth in the Sivathanu et al. article entitled "Structure of Plumes from Burning Aluminized Propellant Estimated using Fan Beam Emission Tomography," *AIAA Journal*, vol. 45, No. 9, pp. 2259-2266, 2007. FIG. 10 shows the local mean temperatures for the flame measured by both emission spectroscopy and the x-ray system 10. The lowest temperatures that can be measured reliably with emission spectroscopy given the level of $CO_2$ concentrations are approximately 1300° K. The system 10 is capable of providing temperatures for the entire range, from a maximum of approximately 1700° K (for the present flame) to as low as 300° K. This is a big advantage of the system 10 over prior methods. The temperatures obtained from the system 10 are therefore believed to be more accurate than that provided by emission spectroscopy. The flame also is seen to have a slightly lower radius, probably due to the effects of confinement by the metal combustor 14.

Figure 11:
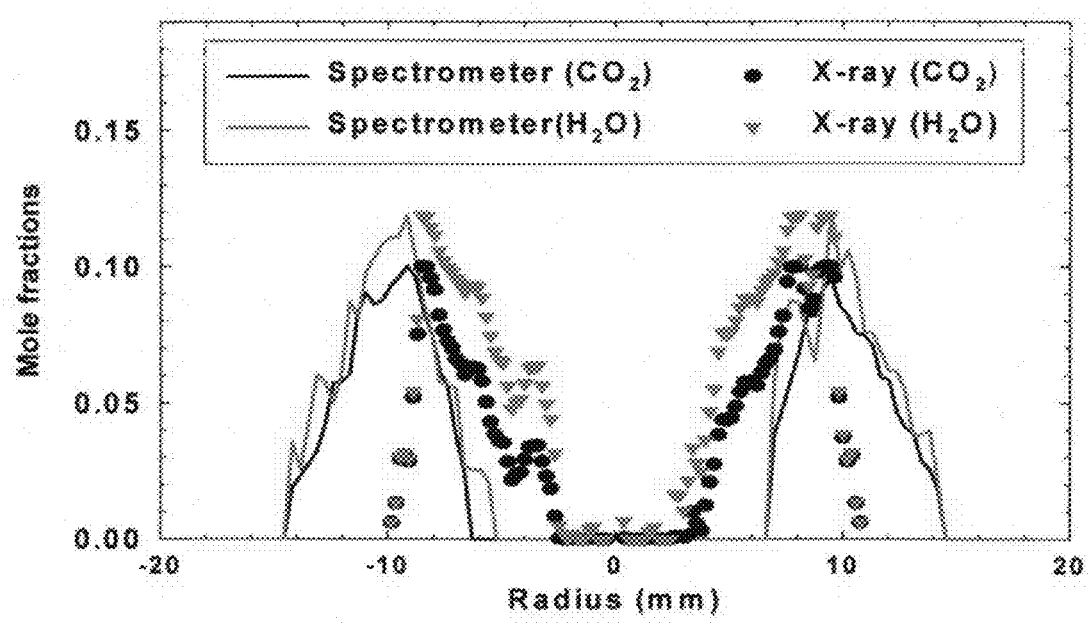
FIG. 11 is a graph of the local mean gas concentrations measured across one plane of the ethylene/argon flame in Example I measured using the present x-ray system in comparison to that measured using a spectrometer.

In addition to temperature, the gas concentrations can also be inferred from the state relationship approach. The gas concentrations obtained from the system 10 and its comparison with the values provided by emission tomography using the procedures of the previously identified Sivathanu et al. article are shown in FIG. 11 in comparison to the x-ray measurements using the system 10. The generally lower concentrations for $CO_2$ are presented in black while the somewhat higher concentrations for $H_2O$ are presented in red. Again, this demonstrates the operability of the system 10 to reliably measure gas concentrations within a closed metal walled area. The various measurements that are possible with the system 10 can accurately reflect various changes in flame structure that result from the insertion of confining barriers or the like into the combustion area.

Example II

Figure 12A:
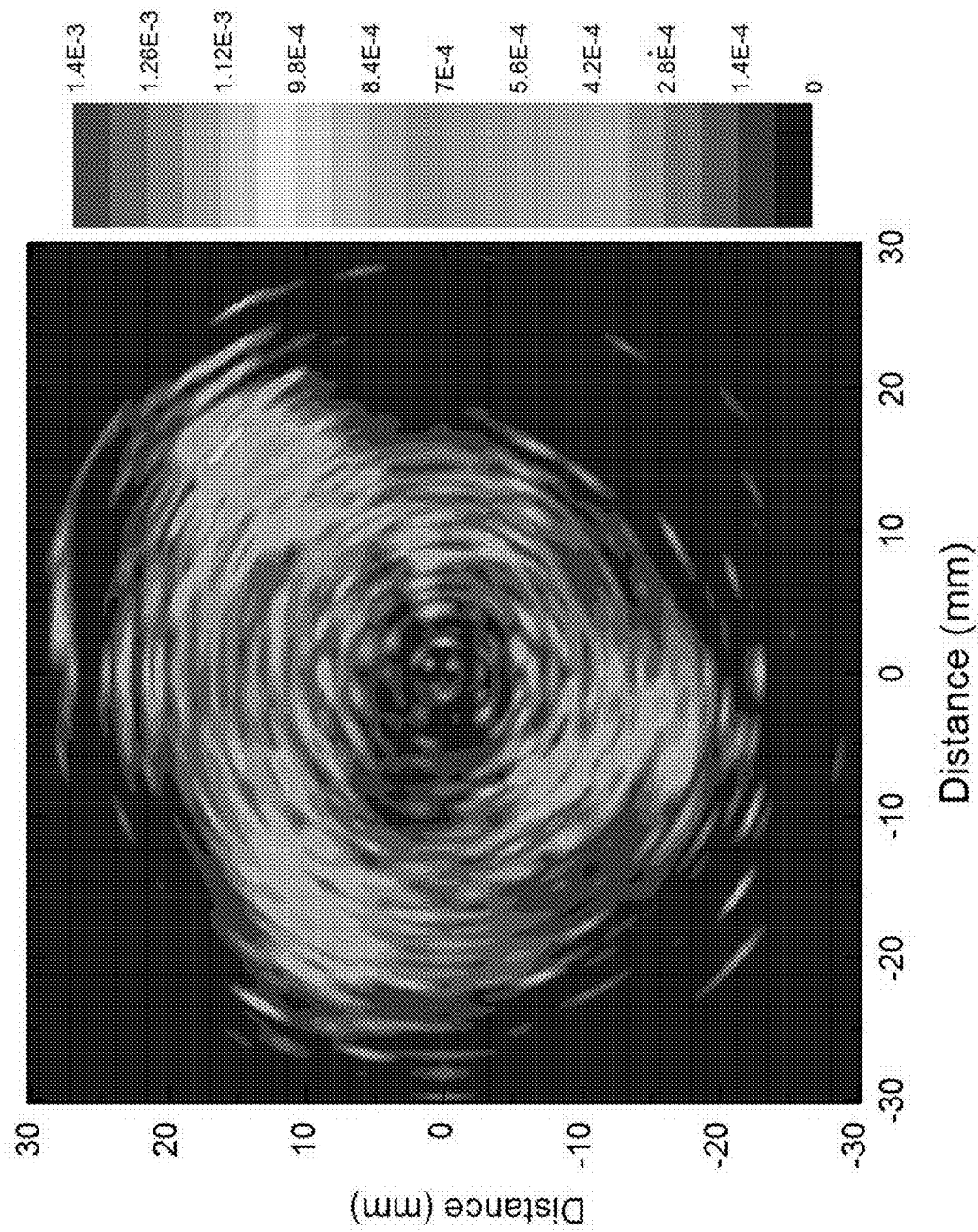
FIG. 12a is a color presentation of the local mass concentrations in one plane of a water spray in Example II measured using the present x-ray system of FIG. 5.

The system 10 was further checked by modifying the system to the form shown in FIG. 5 with a turbulent spray. The turbulent spray head 36 was placed inside the metal combustor 14 and rotated six times so that path integrated absorptances were obtained over six view angles. The data was deconvoluted to provide the spatially and angularly resolved local mass concentrations in one plane of the water spray. To validate the data, the same spray was used (without the metal combustor) in an optical patternator. The optical patternator provides the local surface area density. Though two different quantities (mass concentrations in one and surface area densities in the other) are being compared, the pattern of the spray should be very similar. The planar absorptances of X-Ray energy (in units of 1/mm) for the spray are shown in FIG. 12a. For water sprays with iodide the local absorptances are directly proportional to the local mass concentrations and uniquely determined based on the % of Potassium iodide used in the solution. The color on the plot represents the values shown on the scale to the right of each plot. The surface area density results shown in FIG. 12b were obtained from the turbulent spray using an optical patternator and the method stated in Jongmook Lim and Yudaya Sivathanu, 2005, "Optical Patternation of a Multi-hole Nozzle" Atomization and Sprays, vol. 15, pp. 687-698. It can be immediately seen that the pattern obtained from both methods are very similar. A direct numerical comparison is not possible since different quantities are being measured. The hollow cone feature of the spray and the location of the peak concentrations have been faithfully reproduced using the X-ray system 10.

Figure 13B:
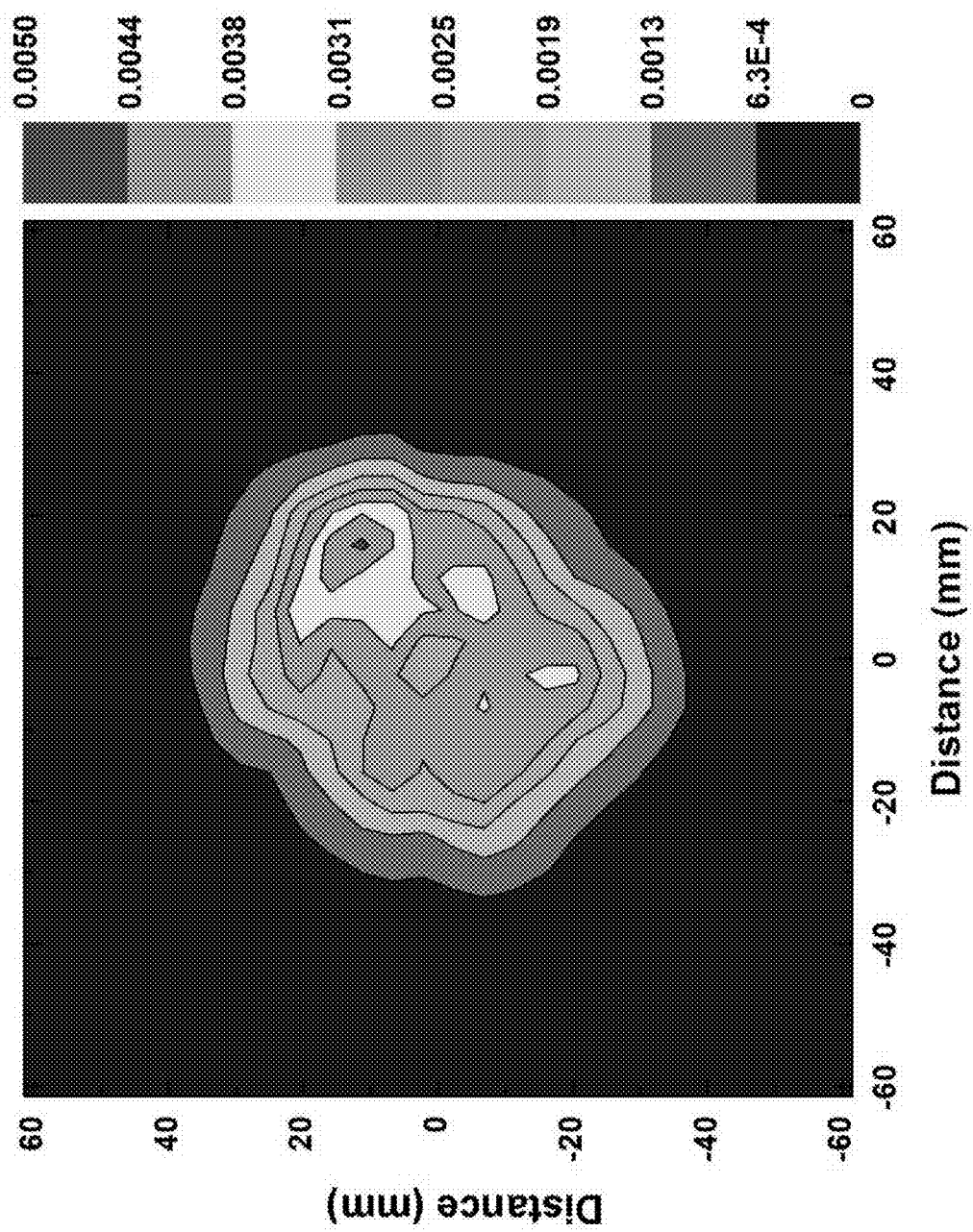
FIG. 13b is a color presentation of the RMS of local surface area density in the same plane of the water spray in Example II measured using an optical patternator.

The RMS of absorptances can also be obtained from the system 10 using the MLE method. The RMS of local absorptances obtained from the system 10 (in units of $mm^{-1}$) is shown in FIG. 13a. The RMS of local surface area densities obtained using the optical patternator is shown in FIG. 13b. The RMS of the mass concentrations (which is directly proportional to the local absorptances) is somewhat different from the RMS of surface area density. Two different quantities are again being measured. Although the source of the difference is not apparent, an important observation available from the spray experiments of this Example is that the system 10 provides qualitatively similar information to the optical patternator for the mean quantity although a dissimilar pattern for the RMS quantity. Therefore, the feasibility of obtaining spray structure information (both mean and RMS) within metal combustors has also been fully demonstrated with the system 10.

Example III

Figure 14:
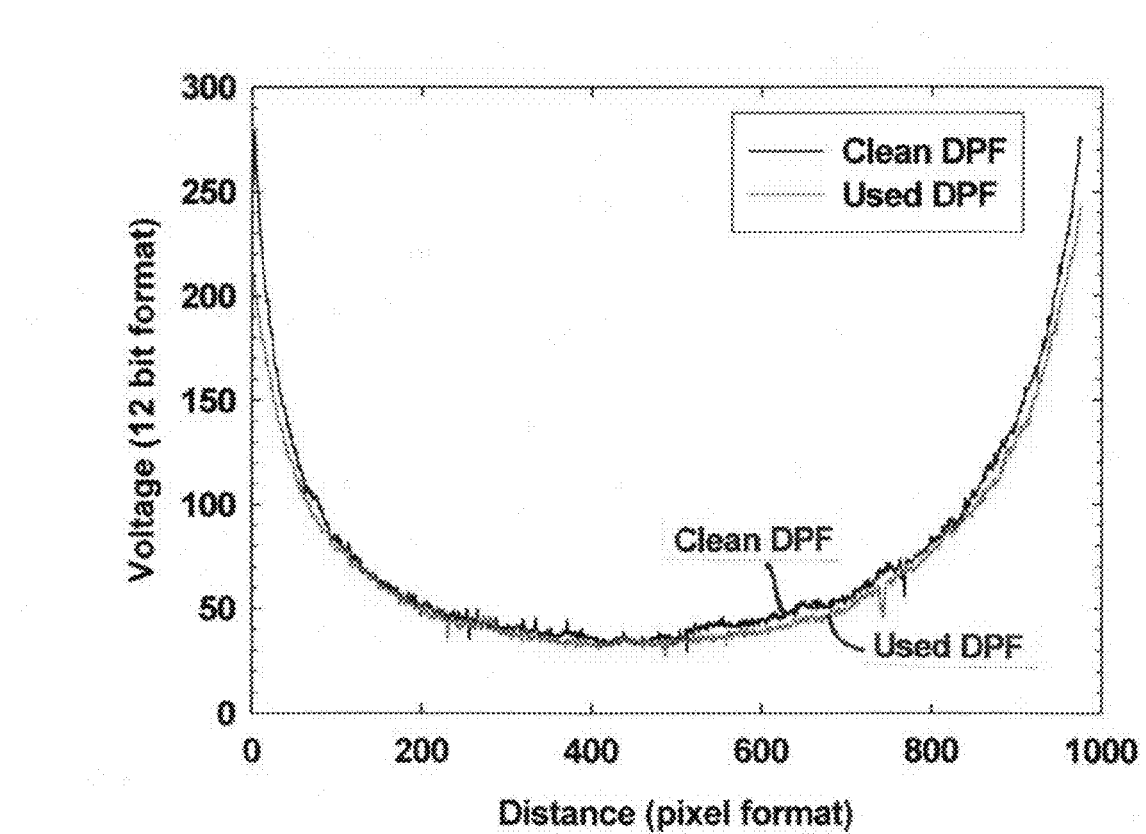
FIG. 14 is a graph of the path integrated transmittances obtained from a new and a used diesel particulate filter used in Example III.
Figure 15:
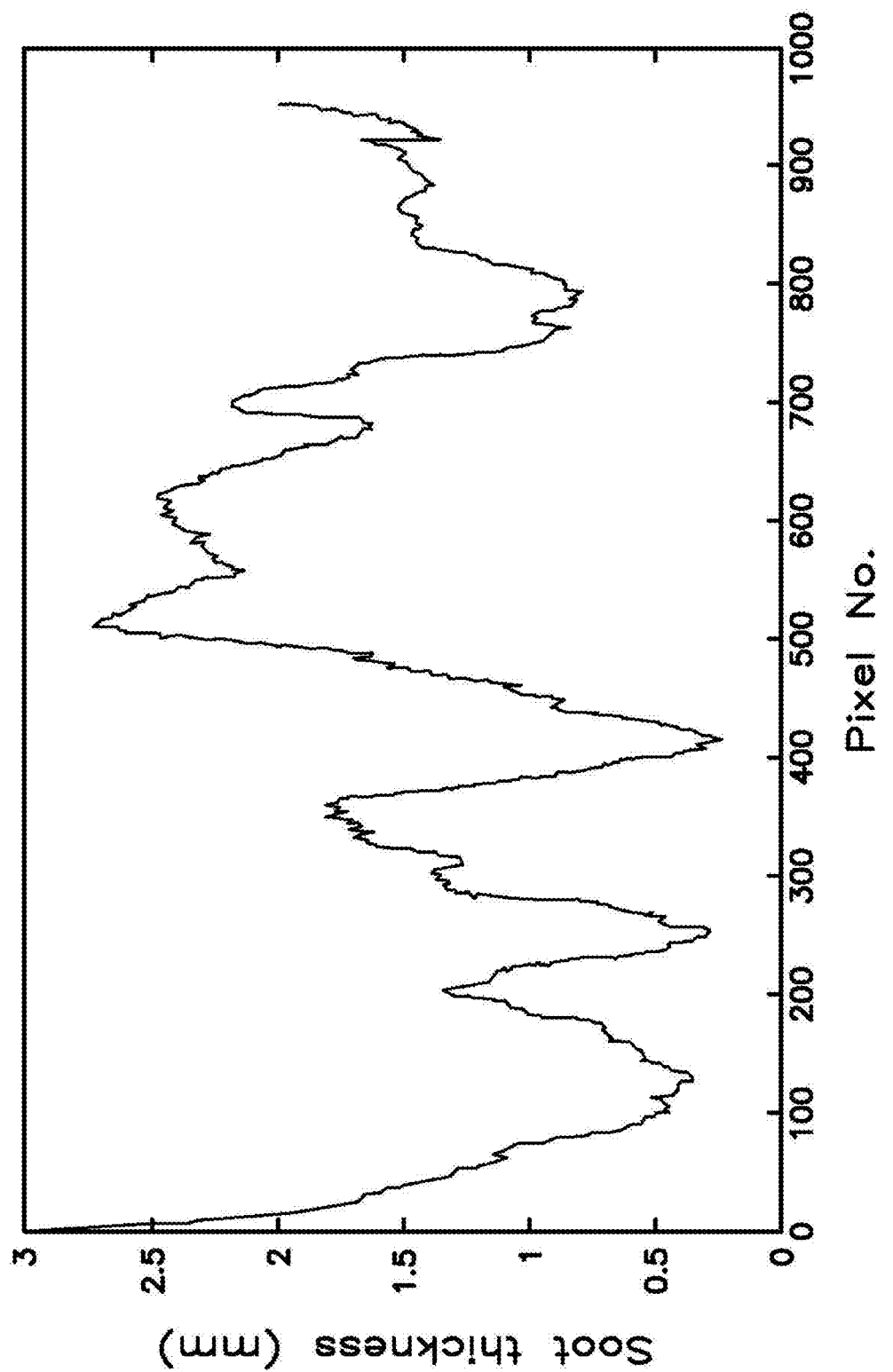
FIG. 15 is a graph of the measured soot thickness in the used diesel particulate filter of Example III based on the deconvolution of the path integrated transmittances shown in FIG. 14.

The system 10 was further checked by substituting a new and a used diesel particulate filter for the volume 12 surrounded by a closed metal wall 14 in the apparatus shown in FIG. 1. The path integrated transmittances from the two diesel particulate filters are shown in FIG. 14. The generally greater path integrated transmittances for the new diesel particulate filer are shown in black while the somewhat smaller path integrated transmittances for the used diesel particulate filer are shown in red. The measurements of the used diesel particulate filter were deconvoluted to provide the local mass of soot. Since only one view angle is available, and the system is not axisymmetric, only the path integrated soot mass distribution was estimated. The estimated path integrated soot thickness is shown in FIG. 15. The asymmetric character of the pattern shown in FIG. 15 reflects the expected character of a used diesel particulate filter and underlines the ability to detect solid particle distributions within a closed metal wall using the system 10.

Example IV

In the system of FIG. 3, there are a total of three arrays arranged in a three-axis arrangement, allowing for a total of approximately 3600 grid elements. Using the system of FIG. 3, the local velocities can be obtained from multi-planar measurements. Image Correlation Velocimetry (ICV) has been used to estimate planar velocities in flows that have distinct visible structures (such as smoke streaks or vortices created with dyes) embedded in the image. The technique can be used even when the camera cannot resolve the individual particles. ICV uses only two shots, or a few shots, to find the pixel-to-pixel correlation, and therefore can be used only when the patterns are very distinct. In a general flow, such as a turbulent spray or flame, such distinct patterns are difficult to discern. Therefore, a statistical image correlation velocimeter (SICV) for estimating velocities in sprays has been developed by Yudaya Sivathanu, Jongmook Lim, Ariel Muliadi , Paul E. Sojka, Yong Chen, Nitin Sharma, and Prabodh Varanasi, "Measurement of Spatially Resolved Mean Velocities in a Transient Spray using Statistical Image Correlation Velocimetry," ILASS Americas, 20th Annual Conference on Liquid Atomization and Spray Systems, Chicago, May 2007. SICV relies on having a very large ensemble of images, but does not require them to have distinct patterns. In addition, the method is relatively straight forward to implement in an industrial setting.

Figure 16A:
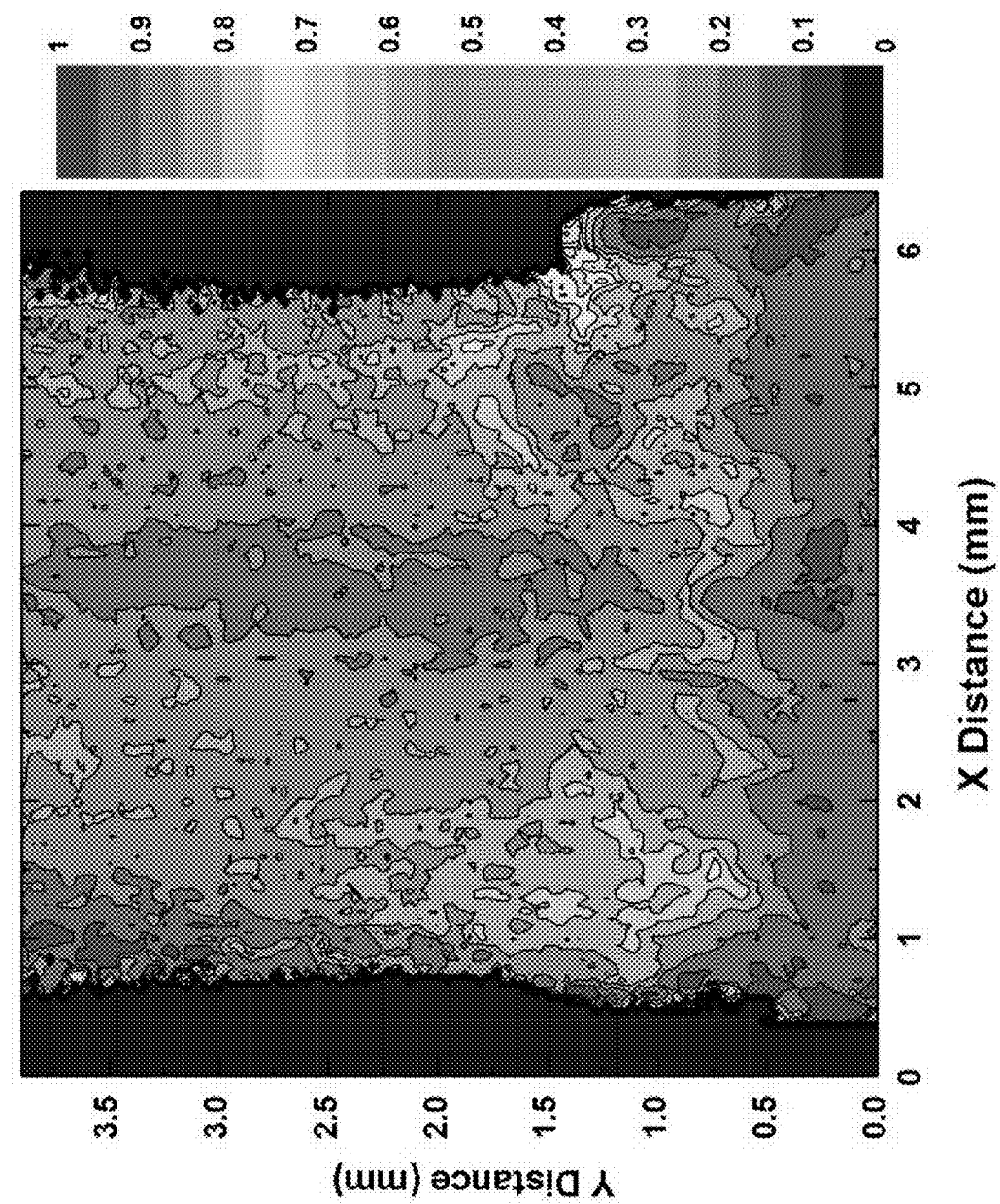
FIG. 16a is a color presentation of the cross correlation coefficients obtained from raw images of a propellant flame using the techniques of Example IV.
Figure 16B:
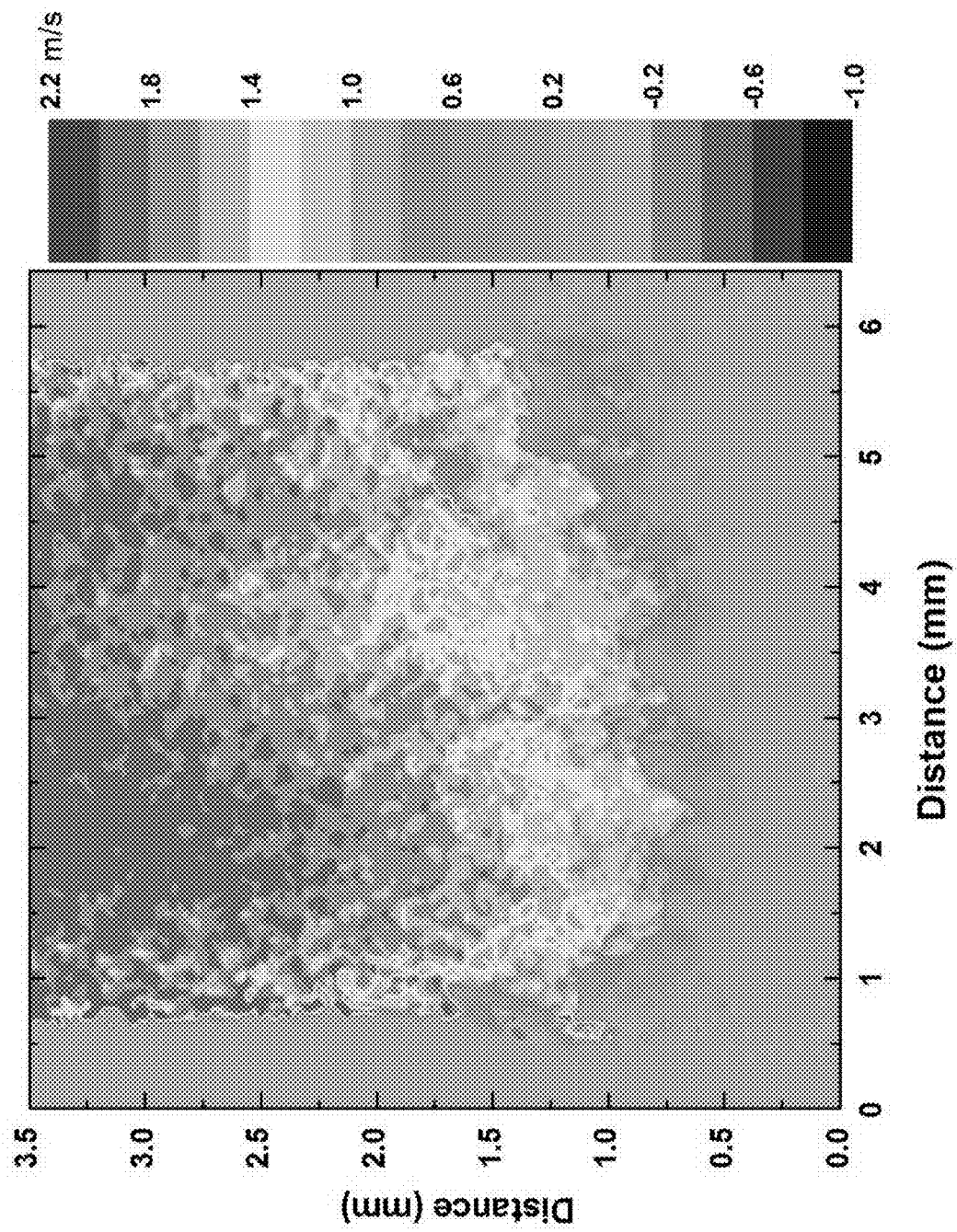
FIG. 16b is a color presentation of the flame velocity observed in a propellant flame using the techniques of Example IV.

From an interrogation of the volume 12 using a multi-planar system 10 such as is shown in FIG. 3, the time series of local absorptances ($\alpha$) are available from the deconvolution algorithm as:

$$\alpha(x, y, z, t) \qquad (2)$$

where x, y, and z are the Cartesian co-ordinates for the measurements. The cross-correlation coefficient between any two points $(x_1,y_1,z_1,t)$ and $(x_2,y_2,z_2,t')$ for a time lag corresponding to t–t' can be obtained as:

$$S = \frac{\int [\alpha(x_1, y_1, z_1, t) - \overline{\alpha(x_1, y_1, z_1)}][\alpha(x_2, y_2, z_2, t') - \overline{\alpha(x_2, y_2, z_2)}]dt}{\sigma_1 \sigma_2} \qquad (3)$$

where the overbar represents the average value, and a is the RMS of local absorptances. The value of S for each $(x_1,y_1,z_1,t)$ is calculated for all values of $(x_2,y_2,z_2,t')$. The location of the maximum value of S defines the average distance moved by the fluid element for the given time lag (t–t'). The ensemble average velocity U (x,y,z,t) is then estimated as the average distance divided by the time lag. It should be noted, that ensemble average velocity can be calculated with any starting time, t. Therefore, transient ensemble average velocities are also captured using the SICV technique. Supporting preliminary data on cross-correlation coefficients and velocities obtained from raw images of a propellant flame are shown in FIG. 16a and FIG. 16b, respectively. The Correlation coefficient in FIG. 16a ranges from a minimum of 0 to a maximum of 1. The velocity ranges from a minimum of 1 m/s to a maximum of 2.2 m/s in FIG. 16b. It can be seen that the correlation coefficient is very high (greater than 0.8) in most locations. At these locations, the velocity data obtained is reliable. The velocities in the center of the plume can reach as high as 2.2 m/s.

The velocities were obtained from imaging an aluminized propellant using a high speed camera. The size of the propellant was 5 mm×5 mm×5 mm.The video was obtained for a period of 5 seconds at 6000 Hz. The initial time t was set to 1 second. It should be noted that when this time is changed to 2, then mean velocities will be obtained 2 seconds after the initiation flame. Therefore, transient ensemble averaged data is possible using the technique. In most areas of the flame, the cross-correlation coefficients exceed 0.9 implying that reliable estimates of velocities can be obtained from the video (Lim and Sivathanu, 2007b). There was a small re-circulation of the flow at the edges of the flame caused by the flame holder. This re-circulation results in a small negative velocity which has been accurately captured by the technique.

As indicated previously, the local extinction coefficients can be converted to temperatures and gas concentrations using standard state relationships. This is possible for most hydrocarbon flames (such as natural gas used in turbine engines, kerosene, heptane, etc.) since state relationships are readily available. For some of the liquid fuels used in automotive engines, such as diesel and gasoline, such state relationships are not available, but can be developed. There are two standard approaches to building state relationships. The first is to use detailed chemical kinetics code and cast the combustion products formed with different mixture ratios into the state relationship format. The second is to utilize a cup burner and obtain the concentrations of the different gas species and temperatures using either emission spectroscopy or gas chromatography. Once the state relationship database is available, then conversion of local extinction coefficients into temperature and gas concentration information in the apparatus 10 of FIG. 6 is straightforward by doping the fuel with argon or xenon so that the mixture fraction evolution can be readily followed.

While these features have been disclosed in connection with the illustrated preferred embodiments, other embodiments of the invention will be apparent to those skilled in the art that come within the spirit of the invention defined in the following claims.

The invention claimed is:

1. A method comprising:
    positioning a plurality of sources of x-rays at a selected location outside a closed, windowless, metal wall surrounding a flow of gas, liquid, or solid particles,
    positioning a plurality of detectors outside the closed metal wall at respective locations suitable to detect x-rays passing entirely through the closed metal wall and a portion of a volume surrounded by the closed metal wall, each of the detectors having a plurality of sensors arranged in at least one row,
    capturing a plurality of respective view angles from the respective detectors to represent a dimensionally distributed view of gas, liquid, or particle density,
    outputting data from the detectors reflecting the distributed view,
    coupling a processor to the output of the detectors to analyze the data,
    detecting, with the processor, variations in gas, liquid or particle density within the volume surrounded by the closed metal wall based on deconvolution of the data by the processor; and
    providing a display to show results of the processor analysis.

2. The method of claim 1, further comprising adding a dopant to the flow of gas.

3. The method of claim 2, wherein the dopant is added to fuel introduced into a burner located within the volume surrounded by the closed metal wall.

4. The method of claim 2, wherein the dopant is added to a liquid used for spraying within the volume surrounded by the closed metal wall.

5. The method of claim 4, wherein the dopant for the liquid comprises potassium iodide.

6. The method of claim 1, further comprising processing the data to correct for any beam hardening of the x-rays as they pass through the closed metal wall.

7. The method of claim 1, wherein the results include a mass concentration of the gas, liquid or solid particles.

8. The method of claim 7, wherein the mass concentration is used to determine a velocity of the flow of gas, liquid or solid particles.

9. A method comprising:
    positioning a plurality of sources of x-rays at a selected location outside a closed, windowless metal wall surrounding a flow of gas,
    positioning a plurality of detectors outside the closed metal wall at locations suitable to detect x-rays passing entirely through the closed metal wall and a portion of a volume surrounded by the closed metal wall, each of the detectors having a plurality of sensors arranged in at least one row,
    adding a dopant to the flow of gas, wherein the dopant consists essentially of one or more noble gases having an atomic number of 86 or less;
    capturing a plurality of respective view angles from the respective detectors to represent a dimensionally distributed view of gas density,
    outputting data from the detectors reflecting the distributed view,
    coupling a processor to the output of the detectors to analyze the data,
    detecting, with the processor, variations in gas density within the volume surrounded by the closed metal wall based on deconvolution of the data by the processor, and
    providing a display to show results of the processor analysis.

10. The method of claim 9, wherein the dopant consists essentially of argon, xenon, or mixtures thereof.

11. A method for detecting variations in gas density within a volume surrounded by a closed metal wall, comprising:
    positioning a plurality of sources of x-rays at a selected location outside the closed metal wall surrounding a flow of gas,
    positioning a detector outside the closed metal wall at a location suitable to detect x-rays passing entirely through a portion of the volume surrounded by the closed metal wall, the detector having a plurality of sensors arranged in at least one row to capture a dimensionally distributed view of detected x-rays and an output providing data reflecting the distributed view,
    coupling a processor to the output of the detector to analyze the data, and providing a display to show results of the processor analysis, and
    processing the data to correct for any beam hardening of the x-rays as they pass through the closed metal wall, the processing comprising:
        filling the volume surrounded by the closed metal wall with a calibration gas having a known absorption coefficient,
        subjecting the volume surrounded by the closed metal wall and calibration gas to x-rays from the plurality of x-ray sources,
        detecting with the detector x-rays that pass through the volume surrounded by the closed metal wall and calibration gas, and
        computing a specific absorption coefficient for the closed metal wall.

12. The method of claim 11, wherein the processing step further comprises repeating the subjecting and detecting steps for different values of x-rays and constructing a look-up table for use by the processor prior to displaying the results of the processor analysis.

13. A method of detecting conditions in a chamber comprising:

arranging a plurality of x-ray sources and a plurality of two-dimensional sensor arrays around a closed, windowless metal chamber having a windowless metal wall with no optical access, supplying the closed metal chamber with a flow of fuel and oxidizer or with a flow of fuel and air, at least one of the fuel, oxidizer or air being doped with an x-ray detectable dopant, receiving, with a processor, data output by the two-dimensional sensor arrays, the data representative of a plurality of view angles from respective sensors included in each of the two-dimensional sensor arrays;

creating, with the processor, a dimensionally distributed map of density of the flow of fuel and oxidizer or the flow of fuel and air by deconvolution of the data received from the two-dimensional sensor arrays, and providing a display to show results of analysis by the processor.

14. The method of claim 13, further comprising using Statistical Image Correlation Velocimetry to obtain data relating to velocity of the flow of fuel and oxidizer or the flow of fuel and air.

15. The method of claim 13, further comprising processing the data to correct for any beam hardening of x-rays as they pass through the metal wall of the closed metal chamber.

16. The method of claim 15, wherein the processing step further comprises filling the closed metal chamber with a calibration gas having a known absorption coefficient, subjecting the closed metal chamber and calibration gas to x-rays from the plurality of x-ray sources, detecting with the sensor arrays, around the closed metal chamber, x-rays that pass through the closed metal chamber and calibration gas, and computing a specific absorption coefficient for the metal wall of the closed metal chamber.

17. A method of detecting conditions in a windowless closed chamber comprising:

arranging a plurality of x-ray sources and a plurality of sensor arrays around a windowless metal wall forming an outside of the closed chamber, the closed chamber having no optical access, supplying the closed chamber with an aerosol of a liquid comprising hydrocarbons, receiving, with a processor, data output by the sensor arrays, the data representative of a plurality of view angles from respective sensors included in each of the sensor arrays;

creating, with the processor, a dimensionally distributed map of density of the aerosol of the liquid by deconvolution of the data received from the sensor arrays; and providing a display to show results of analysis by the processor.

18. The method of claim 17, further comprising processing the data to correct for any beam hardening of x-rays as they pass through the metal wall.

19. The method of claim 18, wherein the processing step further comprises filling the closed chamber with a calibration gas having a known absorption coefficient, subjecting the closed chamber and the calibration gas to x-rays from the plurality of x-ray sources, detecting with the sensor arrays x-rays that pass through the closed chamber and the calibration gas, and computing a specific absorption coefficient for the metal wall of the closed chamber.

20. The method of claim 17, wherein supplying the closed chamber with an aerosol of the liquid further comprises passing x-rays through the metal wall of the closed chamber and the aerosol of the liquid.

* * * * *